US009504750B2

(12) United States Patent
Harel et al.

(10) Patent No.: US 9,504,750 B2
(45) Date of Patent: Nov. 29, 2016

(54) STABILIZING COMPOSITION FOR BIOLOGICAL MATERIALS

(71) Applicant: Advanced BioNutrition Corporation, Columbia, MD (US)

(72) Inventors: Moti Harel, Pikesville, MD (US); Qiong Tang, Columbia, MD (US); Trisha Rice, Columbia, MD (US); Kimberly Jennings, Laurel, MD (US); Brian Carpenter, Baltimore, MD (US); Roger Drewes, Hockessin, DE (US); Elizabeth Raditsis, Columbia, MD (US); January Scarbrough, Silver Spring, MD (US)

(73) Assignee: ADVANCED BIONUTRITION CORPORATION, Columbia, MD (US)

( * ) Notice: Subject to any disclaimer, the term of this patent is extended or adjusted under 35 U.S.C. 154(b) by 0 days.

(21) Appl. No.: 13/849,941

(22) Filed: Mar. 25, 2013

(65) Prior Publication Data
US 2013/0296165 A1 Nov. 7, 2013

Related U.S. Application Data

(63) Continuation-in-part of application No. 13/378,106, filed as application No. PCT/US2011/022821 on Jan. 28, 2011, now Pat. No. 8,834,951, application No. 13/849,941, which is a continuation-in-part of application No. 13/208,459, filed on Aug. 12, 2011.

(60) Provisional application No. 61/373,711, filed on Aug. 13, 2010, provisional application No. 61/614,994, filed on Mar. 23, 2012, provisional application No. 61/642,094, filed on May 3, 2012, provisional application No. 61/646,337, filed on May 13, 2012, provisional application No. 61/299,315, filed on Jan. 28, 2010.

(51) Int. Cl.
A61K 47/26 (2006.01)
A01N 25/22 (2006.01)
A61K 47/36 (2006.01)
A23L 1/30 (2006.01)
A23L 1/305 (2006.01)
A61K 47/42 (2006.01)
A61K 9/19 (2006.01)

(52) U.S. Cl.
CPC .............. A61K 47/42 (2013.01); A01N 25/22 (2013.01); A23L 1/3002 (2013.01); A23L 1/3014 (2013.01); A23L 1/3016 (2013.01); A23L 1/3053 (2013.01); A23L 1/3056 (2013.01); A61K 9/19 (2013.01); A61K 47/26 (2013.01); A61K 47/36 (2013.01)

(58) Field of Classification Search
None
See application file for complete search history.

(56) References Cited

U.S. PATENT DOCUMENTS

| 3,241,977 | A | 3/1966 | Mitchell et al. |
| 3,897,307 | A | 7/1975 | Porubcan |
| 4,337,242 | A | 6/1982 | Markus |
| 4,656,767 | A | 4/1987 | Tarrant |
| 5,227,373 | A | 7/1993 | Alexander |
| 5,262,187 | A | 11/1993 | Hahn |
| 5,407,957 | A | 4/1995 | Kyle |
| 5,518,918 | A | 5/1996 | Barclay |
| 5,637,494 | A | 6/1997 | King |
| 5,658,767 | A | 8/1997 | Kyle |
| 5,715,774 | A | 2/1998 | Adey |
| 5,731,006 | A | 3/1998 | Akiyama |
| 5,766,520 | A | 6/1998 | Bronshtein |
| 5,908,622 | A | 6/1999 | Barclay |
| 5,958,455 | A | 9/1999 | Roser |
| 5,968,569 | A | 10/1999 | Cavadini |
| 5,981,719 | A | 11/1999 | Woiszwillo |
| 6,060,050 | A | 5/2000 | Brown |
| 6,187,330 | B1 | 2/2001 | Wang |
| 6,190,701 | B1 | 2/2001 | Roser et al. |
| 6,258,362 | B1 | 7/2001 | Loudon |
| 6,267,958 | B1 | 7/2001 | Andya et al. |
| 6,290,991 | B1 | 9/2001 | Roser et al. |

(Continued)

FOREIGN PATENT DOCUMENTS

| CA | 2807997 | 2/2012 |
| CL | 9312008 | 3/2008 |

(Continued)

OTHER PUBLICATIONS

Miao, Song, et al. "Effect of disaccharides on survival during storage of freeze dried probiotics." Dairy Science and Technology 88.1 (2008): 19-30.*

(Continued)

Primary Examiner — Abigail Fisher
Assistant Examiner — Daniel Branson
(74) Attorney, Agent, or Firm — RatnerPrestia

(57) ABSTRACT

Dry stabilizing compositions for bioactive materials include sugars and hydrolyzed proteins, and may be formed into tablets or other forms providing enhanced stability for the bioactive material. Compositions containing the bioactive materials may be produced by a method that includes (a) combining the bioactive material with other ingredients in an aqueous solvent to form a viscous slurry; (b) snap-freezing the slurry in liquid nitrogen to form solid frozen particles, beads, droplets or strings; (c) primary drying by water removal under vacuum of the product of step (b) while maintaining it at a temperature above its freezing temperature; and (d) secondary drying of the product of step (c) at maximum vacuum and a temperature of 20° C. or higher for a time sufficient to reduce the water activity to below 0.3 Aw.

20 Claims, 20 Drawing Sheets

(56) References Cited

U.S. PATENT DOCUMENTS

| | | |
|---|---|---|
| 6,306,345 B1 | 10/2001 | Bronshtein et al. |
| 6,331,310 B1 | 12/2001 | Roser et al. |
| 6,338,856 B1 | 1/2002 | Allen |
| 6,338,866 B1 | 1/2002 | Criggall |
| 6,451,567 B1 | 9/2002 | Barclay |
| 6,468,782 B1 | 10/2002 | Tunnacliffe |
| 6,503,411 B1 | 1/2003 | Franks |
| 6,509,146 B1 | 1/2003 | Bronshtein |
| 6,509,178 B1 | 1/2003 | Tanaka |
| 6,534,087 B2 | 3/2003 | Busson et al. |
| 6,537,666 B1 | 3/2003 | Bronshtein |
| 6,565,871 B2 | 5/2003 | Roser et al. |
| 6,582,941 B1 | 6/2003 | Yokochi |
| 6,586,006 B2 | 7/2003 | Roser et al. |
| 6,589,560 B2 | 7/2003 | Foster |
| 6,664,099 B1 | 12/2003 | Worrall |
| 6,716,460 B2 | 4/2004 | Abril |
| 6,726,934 B1 | 4/2004 | Prokop |
| 6,733,759 B2 | 5/2004 | Ivey et al. |
| 6,790,453 B2 | 9/2004 | Porzio et al. |
| 6,797,266 B2 | 9/2004 | Naidu |
| 6,811,792 B2 | 11/2004 | Roser et al. |
| 6,841,181 B2 | 1/2005 | Jager |
| 6,872,357 B1 | 3/2005 | Bronshtein |
| 6,884,866 B2 | 4/2005 | Bronshtein et al. |
| 6,900,173 B2 | 5/2005 | Martin |
| 6,919,172 B2 | 7/2005 | DePablo et al. |
| 6,964,771 B1 | 11/2005 | Roser et al. |
| 7,005,280 B2 | 2/2006 | Barclay |
| 7,052,719 B2 | 5/2006 | Bernstein |
| 7,056,495 B2 | 6/2006 | Roser |
| 7,122,370 B2 | 10/2006 | Porubcan |
| 7,153,472 B1 | 12/2006 | Bronshtein |
| 7,258,873 B2 | 8/2007 | Truong-Le |
| 7,282,194 B2 | 10/2007 | Sung et al. |
| 7,381,425 B1 | 6/2008 | Truong-Le |
| 7,396,548 B2 | 7/2008 | Kyle |
| 7,744,925 B2 | 6/2010 | Roser et al. |
| 7,842,310 B2 | 11/2010 | Hwang |
| 7,927,858 B2 | 4/2011 | Mayeresse |
| 7,939,105 B2 | 5/2011 | Parikh |
| 7,998,502 B2 | 8/2011 | Harel |
| 8,097,245 B2 | 1/2012 | Harel |
| 8,377,496 B2 | 2/2013 | Clinger |
| 8,460,726 B2 | 6/2013 | Harel |
| 8,834,951 B2 | 9/2014 | Harel |
| 8,968,721 B2 | 3/2015 | Harel |
| 9,044,497 B2 | 6/2015 | Harel |
| 9,072,310 B2 | 7/2015 | Harel |
| 2001/0012610 A1 | 8/2001 | Bronshtein |
| 2001/0016220 A1 | 8/2001 | Jager |
| 2002/0192202 A1 | 12/2002 | Naidu |
| 2003/0017192 A1 | 1/2003 | Kanafani |
| 2003/0022333 A1 | 1/2003 | Bronshtein |
| 2003/0165472 A1 | 9/2003 | McGrath et al. |
| 2003/0190332 A1 | 10/2003 | Gilad |
| 2004/0038825 A1 | 2/2004 | Leland |
| 2004/0047881 A1 | 3/2004 | Kyle |
| 2004/0081638 A1 | 4/2004 | Kyle |
| 2004/0081699 A1 | 4/2004 | Rademacher |
| 2004/0175389 A1 | 9/2004 | Porubcan |
| 2004/0177392 A1 | 9/2004 | Barratt et al. |
| 2004/0219206 A1 | 11/2004 | Roser et al. |
| 2004/0241313 A1 | 12/2004 | Nana et al. |
| 2005/0019417 A1 | 1/2005 | Ko |
| 2005/0032192 A1 | 2/2005 | Vesey |
| 2005/0079244 A1 | 4/2005 | Giffard |
| 2005/0100559 A1 | 5/2005 | Myatt |
| 2005/0153018 A1 | 7/2005 | Ubbink |
| 2005/0241011 A1 | 10/2005 | Allnut |
| 2005/0266069 A1 | 12/2005 | Simmons |
| 2006/0008861 A1 | 1/2006 | Allnutt et al. |
| 2006/0024404 A1 | 2/2006 | Kyle |
| 2006/0120999 A1 | 6/2006 | Dhar et al. |
| 2006/0121468 A1 | 6/2006 | Allnutt et al. |
| 2006/0127453 A1 | 6/2006 | Harel |
| 2006/0130162 A1 | 6/2006 | Klye et al. |
| 2006/0147500 A1 | 7/2006 | Klingeberg |
| 2006/0154067 A1 | 7/2006 | Cooper |
| 2006/0222694 A1 | 10/2006 | Oh |
| 2006/0258623 A1 | 11/2006 | Harel |
| 2006/0265766 A1 | 11/2006 | Kyle et al. |
| 2007/0020289 A1 | 1/2007 | Mattern |
| 2007/0031534 A1 | 2/2007 | Tsujimoto |
| 2007/0082008 A1 | 4/2007 | Harel et al. |
| 2007/0207165 A1 | 9/2007 | Thiry |
| 2007/0292952 A1 | 12/2007 | Dhar et al. |
| 2008/0044081 A1 | 2/2008 | Lieb |
| 2008/0044481 A1 | 2/2008 | Harel |
| 2008/0050497 A1 | 2/2008 | Mai et al. |
| 2008/0102132 A2 | 5/2008 | Giner |
| 2008/0131514 A1 | 6/2008 | Truong-Le et al. |
| 2008/0193546 A1 | 8/2008 | Roser et al. |
| 2008/0194504 A1 | 8/2008 | Kyle et al. |
| 2008/0221231 A1 | 9/2008 | Cooper |
| 2008/0229609 A1 | 9/2008 | Bronshtein |
| 2008/0241244 A1 | 10/2008 | Truong-Le |
| 2008/0261916 A1 | 10/2008 | Jaszberenyi |
| 2009/0155351 A1 | 6/2009 | Hejl et al. |
| 2009/0162518 A1 | 6/2009 | Clinger |
| 2009/0162521 A1 | 6/2009 | Clinger |
| 2009/0181363 A1 | 7/2009 | Dhar |
| 2009/0203592 A1 | 8/2009 | Beermann |
| 2009/0208585 A1 | 8/2009 | Roser et al. |
| 2009/0232894 A1 | 9/2009 | Chouvenc et al. |
| 2009/0238890 A1 | 9/2009 | Piechocki et al. |
| 2009/0246184 A1 | 10/2009 | Harel et al. |
| 2009/0324636 A1 | 12/2009 | Piechocki et al. |
| 2010/0015177 A1 | 1/2010 | Drew |
| 2010/0047393 A1 | 2/2010 | Glas |
| 2010/0074994 A1 | 3/2010 | Harel et al. |
| 2010/0086638 A1 | 4/2010 | Kyle et al. |
| 2010/0092521 A1 | 4/2010 | Dhar et al. |
| 2010/0120014 A1 | 5/2010 | Bronshtein |
| 2010/0120676 A1 | 5/2010 | Boehm |
| 2010/0189767 A1* | 7/2010 | Shimoni ............... A23L 1/0029 424/439 |
| 2010/0242301 A1 | 9/2010 | Rampersad |
| 2010/0297231 A1 | 11/2010 | Vehring et al. |
| 2011/0070334 A1* | 3/2011 | Rangavajla .................. 426/61 |
| 2011/0223282 A1 | 9/2011 | Bergonzelli Degonda |
| 2012/0009248 A1 | 1/2012 | Truong-Le et al. |
| 2012/0039956 A1 | 2/2012 | Harel et al. |
| 2012/0040010 A1 | 2/2012 | Harel et al. |
| 2012/0114621 A1 | 5/2012 | Harel |
| 2012/0135017 A1 | 5/2012 | Harel |
| 2012/0288483 A1 | 11/2012 | Harel |
| 2012/0322663 A1 | 12/2012 | Harel |
| 2013/0287896 A1 | 10/2013 | Harel |
| 2013/0296165 A1 | 11/2013 | Harel |

FOREIGN PATENT DOCUMENTS

| | | |
|---|---|---|
| CN | 101287449 A | 10/2008 |
| CN | 101951789 | 1/2011 |
| CN | 102186360 | 9/2011 |
| EP | 0028563 | 5/1981 |
| EP | 0259739 | 3/1988 |
| EP | 471904 A1 | 2/1992 |
| EP | 1110462 | 6/2001 |
| EP | 1344458 | 9/2003 |
| GB | 1 232 057 A | 5/1971 |
| GB | 2389787 | 12/2003 |
| JP | 57114527 | 7/1982 |
| JP | 05246856 | 9/1993 |
| JP | 06-022746 | 2/1994 |
| JP | 11506467 | 6/1999 |
| JP | 11513700 | 11/1999 |
| JP | 2001505431 | 4/2001 |
| JP | 2002530321 | 9/2002 |
| JP | 20044506437 | 3/2004 |
| JP | 2004525106 | 8/2004 |
| JP | 2004528288 | 9/2004 |
| JP | 2005501268 | 1/2005 |

(56) References Cited

FOREIGN PATENT DOCUMENTS

| | | |
|---|---|---|
| JP | 2005519600 | 7/2005 |
| JP | 2005270100 | 10/2005 |
| JP | 2005534741 | 11/2005 |
| JP | 2007519796 | 7/2007 |
| JP | 2007522085 | 8/2007 |
| JP | 2009522280 | 6/2009 |
| JP | 2010512755 | 4/2010 |
| KR | 20050105669 | 11/2005 |
| KR | 1020050106559 | 11/2005 |
| WO | 9527721 | 10/1995 |
| WO | 9640077 | 12/1996 |
| WO | 9824882 | 6/1998 |
| WO | WO 98/24327 | 6/1998 |
| WO | 0032064 | 6/2000 |
| WO | 0112779 | 2/2001 |
| WO | 0136590 | 5/2001 |
| WO | 0215720 | 2/2002 |
| WO | 02058735 | 8/2002 |
| WO | 02061111 | 8/2002 |
| WO | 02076391 | 10/2002 |
| WO | 03086454 | 10/2003 |
| WO | 03088755 | 10/2003 |
| WO | 03089579 | 10/2003 |
| WO | WO 03/103692 | 12/2003 |
| WO | 2004022728 | 3/2004 |
| WO | 2004024177 | 3/2004 |
| WO | 2004039417 | 5/2004 |
| WO | WO 2004/043139 | 5/2004 |
| WO | 2004080196 | 9/2004 |
| WO | WO 2004/091307 | 10/2004 |
| WO | 2004112767 | 12/2004 |
| WO | 2004112776 | 12/2004 |
| WO | 2005030229 | 4/2005 |
| WO | WO 2005/060937 A1 | 7/2005 |
| WO | 2005084646 | 9/2005 |
| WO | 2005105978 | 11/2005 |
| WO | 2005115341 | 12/2005 |
| WO | 2005117962 | 12/2005 |
| WO | 2006085082 | 8/2006 |
| WO | 2006122299 | 11/2006 |
| WO | 2007035455 | 3/2007 |
| WO | WO 2007/038926 A1 | 4/2007 |
| WO | WO 2007/067207 | 6/2007 |
| WO | 2007075988 | 7/2007 |
| WO | 2007084059 | 7/2007 |
| WO | 2007084500 | 7/2007 |
| WO | WO 2007/079147 A2 | 7/2007 |
| WO | 2007117511 | 10/2007 |
| WO | 2007136553 | 11/2007 |
| WO | 2008016214 | 2/2008 |
| WO | 2008056983 | 5/2008 |
| WO | 2008076975 | 6/2008 |
| WO | 2009002481 | 12/2008 |
| WO | WO 2009/140327 | 11/2009 |
| WO | WO 2010/002418 A2 | 1/2010 |
| WO | 2010046321 | 4/2010 |
| WO | WO 2010/111347 | 9/2010 |
| WO | WO 2010/118188 | 10/2010 |
| WO | WO 2010/118205 | 10/2010 |
| WO | WO 2010/135495 A2 | 11/2010 |
| WO | WO 2010/138522 A2 | 12/2010 |
| WO | WO 2011/094469 | 8/2011 |

OTHER PUBLICATIONS

Santivarangkna, Chalat, et al. "Role of Glassy State on Stabilities of Freeze-Dried Probiotics." Journal of food science 76.8 (2011): R152-R156.*
Annear, D.I., "The Preservation of *Leptospires* by Drying from the Liquid State," J. Gen. Microbiol. (1962), 27, 341-343.
Capela, P. et al., "Effect of cryoprotectants, prebiotics and microencapsulation on survival of probiotic organisms in yoghurt and freeze-dried yoghurt," Food Research International (2006), 39, 203-211.
Crowe, J.H. et al., 1983, *Cryobiology*, 20, 346-356.
Crowe, J.H., "The Role of Vitrification in Anhydrobiosis," Annu. Rev. Physiol. (1998), 60, 73-103.
Esquisabel et al., 1997, *J. Microencapsulation*, 24, 627-638.
First Office Action with a Search Report issued by the State Intellectual Property Office of the People's Republic of China on May 22, 2013 for Chinese Application No. 201180007562.3.
International Preliminary Report on Patentability for PCT International Application No. PCT/US2011/022821 dated Jul. 31, 2012.
Kets et al. ("Citrate increases glass transition temperature of vitrified sucrose preparations," Cryobiology 48 (2004) 46 54).
M. Le Meste, et al., 2002, Glass Transition and Food Technology: A Critical Appraisal, *Journal of Food Science*, 67:2444-2458.
Morgan, C.A., "Preservation of micro-organisms by drying; a review," Journal of Microbiological Methods, (2006), 66, 183-193.
Sanchez et al., 1999, *Intl. J. Pharm. 185*, p. 255-266.
Supplementary European Search Report dated Sep. 18, 2013 for European Appl. No. 11737688.9.
Tobar et al., Oral Vaccination of Atlantic Salmon Salmo salar against Salmonid rickettsial septicaemia (SRS), abstract, World Aquaculture Society's 2008 annual international conference (May 19-23, 2008).
Tobar et al., Oral Vaccination of Atlantic Salmon Salmo salar against Salmon Rickettsial Septicaemia, presentation, World Aquaculture Society's 2008 annual international conference (May 19-23, 2008).
Wong, T.W., "Chitosan and its use in design of insulin delivery system," Recent Patents on Drug Delivery & Formation (2009), 3, pp. 1720-1723.
Zarate et al.,("Viability and biological properties of probiotic vaginal lactobacilli after lyophilization and refrigerated storage into gelatin capsules," Process Biochemistry 41 (2006) 1779-1785).
Abdelwahed et al., "Freeze-drying of nanoparticles: Formulation, process and storage considerations" Advanced Drug Delivery Reviews, (2006), vol. 58, pp. 1688-1713.
Desai et al. "Gastrointestinal Uptake of Biodegradable Microparticles: Effect of Particle Size" Pharmaceutical Research (1996), vol. 1, Issue 12, pp. 1838-1845.
Notice of Allowance mailed Jan. 15, 2015 in U.S. Appl. No. 13/911,636.
Office Action mailed Jan. 14, 2015 in U.S. Appl. No. 13/321,708.
Russian Office Action mailed Dec. 18, 2014 in Appl. No. 2011151788/10(077759).
Benedict, R. G. et al., "Preservation of Microorganisms by Freeze-Drying I Cell Supernatant, Naylor-Smith Solution, and Salts of Various Acids as Stabilizers for Serratia marascens," Appl. Microbiol. 1958, vol. 6, No. 6, pp. 401-407.
European Office Action for Application No. 10 781 100.2-1403 dated Oct. 17, 2014.
Extended European Search Report for European Application No. 11817090.1-1358 dated Jun. 16, 2014.
International Search Report for International Application No. PCT/US2010/036098 mailed Feb. 14, 2011.
International Search Report for International Application No. PCT/US2011/022821 mailed Oct. 25, 2011.
Maltrin M100 Maltodrexin, 2006, XP055120984, Internet retrieves from the Internet: URL: http://www.tpipremixes.com/productpdfs/Maltodextrin.pdf, retrieved on Jun. 2, 2014.
Perry, Stephen F, "Freeze-Drying and Cryopreservation of Bacteria," Molecular Biotechnology, 1998, vol. 9, No. 1, pp. 59-64.
Entire prosecution history of U.S. Appl. No. 14/456,130, filed Aug. 11, 2014, entitled, "Dry Glassy Composition comprising a Bioactive Material."
Entire prosecution history of U.S. Appl. No. 14/479,791, filed Sep. 8, 2014, entitled, "Dry Food Product Containing Live Probiotic."
Anal et al. "Recent advances in microencapsulation of probiotics for industrial applications and targeted delivery." Trends in Food Science and Technology, vol. 18, No. 5, Apr. 29, 2007, pp. 240-251.
Anderson, J.W., Johnstone, B.M. and Beasley, D.T. (1999). Breastfeeding and cognitive development: a meta-analysis. Am J Clin Nutr, 70, 525-35.
Bazan, N.G. and Rodriguez de Turco E.B. (1994), Review: pharmacological manipulation of docosahexaenoic-phospholipid bio-

(56) References Cited

OTHER PUBLICATIONS synthesis in photoreceptor cells: implications in retinal degeneration. J. Ocul Pharmacol, 10, 591-604.
Bazan, N.G. and Scott, B.L. (1990). Dietary omega-3 fatty acids and accumulation of docosahexaenoic acid in rod photoreceptor cells of the retina and at synapses. Ups J Med Sci Suppl, 48. 97-107.
Behrens, P. and Kyle, D, (1996). Microalgae as a source of fatty acids. J Food Sci, 3, 259-272.
Bergogne et al., Molecular Crystals and Liquid Crystals, 354: 79-89 (2000).
Boswell KDB, Gladue R, Prima B, Kyle DJ (1992) SCO production of fermentive microalgae. In: Kyle DJ, Ratledge C (eds) Industrial Applications of Single Cell Oils. American Oil Chemists Society, Champaign, IL., pp. 274-286.
Canadian Office Action mailed Apr. 6, 2011 in Canadian Application No. 2,673,120.
Chen, et al., "Beneficial Effect of Intracellular Trehalsose on the Membrane Integrity of Dried Mammalian Cells", Cryobiology vol. 43, pp. 168-181, 2001.
Chen et al., China Tropical Medicine, 7(4):654-55 (2007) (with partial English ranslation).
Chinese Search Report dated May 26, 2014 for application No. 201180039219.7 filed Aug. 12, 2011.
Crawford, M.A., Costeloe, K., Ghebremeskel, K. and Phylactos, A. (1998). The inadequacy of the essential fatty acid content of present preterm feeds [published erratum appears in Eur J. Pediatr Feb. 1998; 157(2):160]. Eur J Pediatr. 157 Suppl 1, S23-7.
Crowe et al., "Anhydrobiosis: A Strategy for Survival", Adv. Space Res vol. 12, No. 4, pp. 239-247, 1992.
De Giulio, et al., "Use of alginate and cryo protective sugars to improve the viability of lactic acid and bacteria after freezing and freeze-drying" ,World Journal of Microbiology and Biotechnology, Kluwer Academic Publishers, DO, vol. 21, No. 5, Jul. 1, 2005, pp. 739-746.
Entire patent prosecution history of U.S. Appl. No. 12/519,860, filed, Dec. 2, 2009, entitled, "Dry Food Product Containing Live Probiotic," now U.S. Pat. No. 8,460,726.
Entire prosecution history of U.S. Appl. No. 12/159,407, filed Nov. 21, 2008, entitled , "Delivery Vehicle for Probiotic Bacteria Comprising a Dry Matrix of Polysaccharides, Saccharides and Polyols in a Glass Form and Methods of Making Same," now U.S. Pat. No. 8,097,245.
Entire prosecution history of U.S. Appl. No. 13/208,459, filed Aug. 12, 2011, entitled, "Dry Storage Stabilizing Composition for Biological Materials."
Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making."
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same."
Entire prosecution history of U.S. Appl. No. 13/378,106, filed Mar. 29, 2012, entitled, "Dry Glassy Composition Comprising a Bioactive Material," now U.S. Pat. No. 8,834,951.
Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same."
Entire prosecution history of U.S. Appl. No. 13/911,636, filed Jun. 6, 2013, entitled, "Dry Food Product Containing Live Probiotic."
Favaro-Trindade et al., "Microencapsulation of L. acidophilus (La-05) and B. lactis (Bb-12) and evaluation of their survival at the pH values of the stomach and in bile", J. Microencapsulation, vol. 19, pp. 485-494, 2002.
Grinstead G, Tokach M, Dritz, S. Goodband R, Nelssen J (2000) Effects of Spirulina platensis on growth performance of weanling pigs. Animal Feed Sci Technol 83:237-247.

He Ml, Hollwich W. Rambeck WA (2002) Supplementation of algae to the diet of pigs: a new possibility to improve the iodine content in the meat. J Animal Physiol Animal Nutri 86:97-104.
Hincha, D., et al., "Protection of liposomes against fusion during drying by oligosaccharides is not predicted by the calorimetric glass transition temperatures of the dry sugars," European Biophysics Journal, 37 (2008) 503-508.
Hughes, V.X. and Hillier, S.L. (1990). "Microbiologic characteristics of Lactobacillus products used for colonization of the vagina." Obstet Gynecol. 75:244-248.
Ikemoto, A., Kobayashi, T., Watanabe, S. and Okuyama, H. (1997). Membrane fatty acid modifications of PC12 cells by arachidonate or docosahexaenoate affect neurite outgrowth but not norepinephrine release. Neurochem Res, 22, 671-8.
International Search Report for International Application No. PCT/US2006/49434 dated Sep. 26, 2007.
International Search Report for International Application No. PCT/US2007/087771 mailed May 16, 2008.
Japanese Office Action for Japanese Patent Application No. 2008-548729, mailed Jul. 23, 2012 (with English translation).
Japanese Office Action issued in Japanese Application No. 2013-524242, dated Jan. 21, 2014 (English tranisation only).
Japanese Office Action mailed Aug. 1, 2014 in Japanese Application No. 2012-513183, with translation (with English Translation).
Kailasapathy et al., "Survival and therapeutic potentia of probiotic organisms with reference to Lactobacillus acidophilus and Bifidobacterium spp.," Immunology Cell Biology, 78, pp. 80-88, 2000.
Kearney, et al., "Enhancing the Viability of Lactobacillus plantarum Inoculum by Immobilizing the Cells in Calcium-Alginate Beads Incorporation Cryoprotectants", Applied and Environmental Microbiology, vol. 56, No. 10, Oct. 1990, pp. 3112-3116.
Krallish et al., "Effect of xylitol and trehalose on dry resistance of yeasts", Appl. Microbiol Biotechnol. 47, pp. 447-451, 1997.
Krasaekoopt et al. "Evaluation of encapsulation techniques of probiotics for yoghurt." International Dairy Journal 13, 2003. pp. 3-13.
Liao et al., "Protective Mechanism of Stabilizing Excipients against Dehydration in the Freeze-Drying of Proteins", Pharmaceutical Research, vol. 19, No. 12, pp. 1854-1861, 2002.
Linders et al., "Effect of Added Carbohydrates on Membrane Phase Behavior and Survival of Dried Lactobacillus plantarum" , Cryobiology 35, pp. 31-40, 1997.
Marteau et al., "Protection from gastrointestinal diseases wth the use of probiotcs", Am J Clin Nutr. 73, pp. 430S-436S, 2001.
Martinez, M. (1990). Severe deficiency of docosahexaenoic acid in peroxisomal disorders: a defect of delta 4 desaturation. Neurology, 40, 1292-8.
Mazur et al., Hydration of Sodium Alginate in Aqueous Solution, Macromolecules, (2014) 47: 771-776.
New Zealand Examination Report dated May 18, 2012 in New Zealand Application No. 597053.
Niness, Inulin and Olgifructose: What are they?., J. Nutr. 129, 1999, pp. 1402S-1406S.
Office Action dated Mar. 21, 2014 in Russian patent application No. 2011151788/10(077759) (with English translation).
Office Action for Patent Application JP 2009-541634 mailed Jun. 25, 2012 (with English translation).
Office Action mailed Aug. 6, 2014 in Russian Application No. 2011151788/10 (077759) (with English Translation).
Perdigon et al, "Lactic Acid Bacteria and their Effect on the Immune System", Curr Issues Intest Microbiol. 2, pp. 27-42, 2001.
Qiu et al. "Permeability of the infective juveniles of Steinernema carpocapsae to glycerol during osmotic dehydration and its effect on biochemical adaptation and energy metabolism" , Comparative Biochemistry & Physiology, Part B, vol. 125, pp. 411-419, 2000.
Schwab, C. et al., "Influence of oligosaccharides on the viability and membrane properties of lactobacillus reuteri TMW1,106 during freeze-drying," Cryobiology, 55 (2007) 108-114.
Second Office Action issued by the State Intellectual Property Office of the Peoples Republic of China Feb. 8, 2014 in Chinese Application No. 201180075E0, including a Search Report (with English translation).

(56) References Cited

OTHER PUBLICATIONS

Selmer Olsen, et al., "Survival of Lactobacillus helveticus entrapped in Ca-alginate in relation to water content, storage and rehydration", Journal of Industrial Microbiology & Biotechnology, vol. 23, 1999, pp. 79-85.
Shah, N.P. (2000). "Probiotic bacteria: selective enumeration and survival in dairy foods." Journal of Dairy Science. 83:894-907.
Shin et al., Growth and Viability of Commerical Bifidobacterium spp in Skim Milk containing oligosaccharides and Inulin, Journal of Food Science, 2000, vol. 65, No. 5, pp. 884-887.
Stordy BJ. (1995). Benefit of docosahexaenoic acid supplements to dark adaptation in dyslexics. Lancet, 346 (8971): 385.
Substantive Examination Adverse Report mailed Aug. 29, 2014 in Malaysian Application No. PI 2011005733.
Sucrose, Sucrose structure, Webpage, Elmhurst College, 2003.
Supplementary European Search report in European Application No. EP 10781100.2-2405 dated Oct. 9, 2012.
Isolauri et al., "Probiotics: effects on immunity", Am J Clin Nutr. 73, pp. 444S-450S, 2001.
Xu, L.Z., Sanchez, R., Sali, A. and Heintz, N. (1996). Ligand specificity of brain lipid-binding protein. J Biol Chem, 271, 24711-9.
Extended European Search Report for European Application No. 13764138.7-1460 dated Apr. 9, 2015.
Japanese Office Action issued Mar. 31, 2015 in Japanese Application No. 2012-513183.
Australian Patent Examination Report dated Jan. 23, 2015 in Patent Application No. 2010254235.
Japanese Office Action issued Mar. 2, 2015 in Japanese Application No. 2012-551295.
Chinese Office Action mailed Mar. 2, 2015 in Chinese Application No. 201180007562.3.
Notice of Allowance mailed Oct. 27, 2014 in U.S. Application No. 13/459,408.
Office Action mailed Oct. 27, 2014 in U.S. Appl. No. 13/208,459.
International Preliminary Report on Patentability and Written Opinion for PCT International Application No. PCT/US2013/033505 issued Sep. 23, 2014.
Canadian Office Action mailed Oct. 10, 2014 in Canadian Application No. 2,785,815.
Japanese Office Action mailed Sep. 15, 2015 for Japanese Application No. 2012-513183, including English translation.
Singapore Search Report and Written Opinion mailed Sep. 9, 2015 for Application No. 11201405478V.
Substantive Examination Adverse Report mailed Sep. 15, 2015 in Malaysian Application No. PI 2013000306.
Japanese Office Action issued Oct. 7, 2015 in Japanese Application No. 2012-551295, including English translation.
Mexican Office Action mailed Jul. 20, 2015 in Mexican Application No. MX/a/2012/008795.
New Zealand Office Action mailed Jun. 24, 2015 in New Zealand Application No. 628912.
Russian Office Action mailed Jul. 21, 2015 in Russian Application No. 2013110833/13.
Substantive Examination Adverse Report mailed Jun. 30, 2015 in Malaysian Application No. PI 2011005733.
Office Action mailed Jun. 30, 2015 in Vietnamese Application No. 1-2011-03487.
Aral, C. et al., "Alternative approach to the preparation of chitosan beads," International Journal of Pharmaceutics 168 (1998) 9-15.
Bodmeier, R., et al., "Preparation and evaluation of drug-containing chitosan beads," Drug Development and Industrial Pharmacy, 15(9), 1989, 1475-1494.
Bradford, M., "A rapid and sensitive method for the quantitation of microgram quantities of protein utilizing the principle of protein-dye binding," Analytical biochemistry 72 (1976) 248-254.
Calvo, P., et al., "Novel hydrophilic chitosan-polyethylene oxide nanoparticles as protein carriers," Journal of Applied Polymer Science, 63 (1997) 125-132.
Canadian Office Action mailed Sep. 8, 2015 for Canadian Application No. 2,785,815.
Chopra, S. et al., 2006. Advances and potential applications of chitosan derivatives as mucoadhesive biomaterials in modern drug delivery, J. Pharm. Pharmacol. 58(8). 1021-1032.
Dang, J.M., Leong, K.W., 2006. Natural polymers for gene delivery and tissue engineering. Adv. Drug Deliv. Rev. 58(4), 487-499.
Davis, S.S., 2006. The use of soluble polymers and polymer microparticles to provide improved vaccine responses vaccine responses after parenteral and mucosal delivery. Vaccine 24(2), 7-10.
Entire patent prosecution history of U.S. Appl. No. 13/260,661, filed Nov. 2, 2011, entitled, "Microparticulated Vaccines for the Oral or Nasal Vaccination and Boostering of Animals Including Fish."
European Office Action mailed Nov. 6, 2015 for European Application No. 11817090.1.
Examination Report on Patent Application for Chilean Application No. 759-09 hated Mar. 27, 2009.
Huang, Y.C., et al., "Optimizing formulation factors in preparing chitosan microparticles by spray-drying method," Journal of Microencapsulation, vol. 20, No. 2 (2003) 247-260.
International Search Report for Application No. PCT/US2010/028767 dated Dec. 23, 2010.
Kang, M.L. et al., Pluronic F127 enhances the effect as an adjuvant of chitosan microspheres in the intranasal delivery of Bordeteila bronchiseptica antigens containing dermonecrotoxin. Vaccine 25(23), 4602-4610.
Kim, T. J. et al., 2007. Stimulation of mucosal and systemic antibody responses against recombinant transferrin-binding protein B of Actinobacillus pleuropneumoniae with chitosan after tracheal administration in piglets, J. Vet. Med. Sci. 69(5), 535-539.
Li, et al., "Preparation of alginate coated chitosan micropartieles for vaccine delivery," BMC Biotechnology 8:89 (2008).
Malik, D.K., et al., 2007. Recent advances in protein and peptide drug delivery systems. . Curr. Drug Deliv. 4(2), 141-151.
Non-Final Office Action mailed Oct. 27, 2015 in U.S. Appl. No. 13/208,459.
Panos, I., et al., "New drug delivery systems based on chitosan," Current Drug Discovery Technologies, 5 (2008) 333-341.
Rege, P., et al., "Spray-dried chitinosans Part I: preparation and characterization," International Journal of Pharmaceutics 252 (2003) 41-51.
Shiraishi, S., et al,. "Controlled retease of indomethacin by chitosan-polyelectrolyte complex: optimization and in vivo/in vitro evaluation," Journal of Controlled Release 25 (1993) 217-225.
Shu, X., et al., "A novel approach to prepare tripolyphosphate/chitosan complex beads for controlled release drug delivery," International Journal of Pharmaceutics 201 (2000) 51-58.
Tobar et al., Oral vaccination of Salmo salar against Salmon Rickettsial Septicaemia, World Aquaculture Society's 2008 annual international conference (May 19-23, 2008).
van der Lubben, I.M., et al., 2001. Chitosan microparticles for oral vaccination: preparation, characterization and preliminary in vivo uptake studies in murine Peyer's patches, Biomaterials 22(7), 687-694.
van der Lubben, I.M., et al., 2001. Chitosan for mucosal vaccination. Advanced Drug Delivery Reviews 52 (2), 139-144.
Zhou, S., et al., "Poly-D, L-lactide-co-poly(ethylene glycol) microspheres as potential vaccine delivery systems," Journal of Controlled Release 86 (2003) 195-205.
Non Final Office Action mailed Jan. 12, 2016 for U.S. Appl. No. 14/479,791.
Canadian Office Action mailed Dec. 8, 2015 for Canadian Application No. 2,756,883.
Chinese Reexamination Report dated Dec. 23, 2015 for Chinese Application No. 201080029392.4 with translation.
Canadian Office Action dated Mar. 10, 2016 for Canadian Application No. 2,763,074.
Chinese Office Action dated Feb. 26, 2016 for Chinese Application No. 201380015928.0 with translation.
Chinese Search Report dated Feb. 23, 2016 for Chinese Application No. 2013800115928.0 with translation.

(56) References Cited

OTHER PUBLICATIONS

Chinese Office Action dated Apr. 1, 2016 for Chinese Application No. 201410326898.1 with translation.
Philippines Substantive Examination Report dated Apr. 15, 2016 for Philippines Application No. 1-2012-501410.
Non Final Office Action dated Jan. 22, 2016 for U.S. Appl. No. 13/321,708.
Non Final Office Action mailed Feb. 3, 2016 for U.S. Appl. No. 14/456,130.
Phiiippine Office Action dated Jan. 14, 2016 for Philippine Application No. 1-2011-502445.
European Office Action for European Application No. 10756894.1, dated Jun. 22, 2016, 5 pages.
Notification of Reexamination of Chinese Application No. 201080029392.4, dated Jul. 13, 2016, 10 pages.
European Examination Report for EP Application No. 11817090.1, dated Jul. 15, 2016, 6 pages.
Indonesian Examination Report for Indonesian Application No. W00 2013 00512, dated Jun. 30, 2016, 4 pages.
Indonesian Examination Report for Indonesian Application No. W00 201104583, dated Jun. 27, 2016, 4 pages.
Mexican Office Action for Mexican Application No. MX/a/2013/001535, dated Jul. 13, 2016 with translation, 4 pages.
Non Final Office Action for U.S. Appl. No. 14/644,248, mailed Jul. 15, 2016, 58 pages.
Final Office Action for U.S. Appl. No. 13/260,661, mailed Jun. 1, 2016, 48 pages.
Final Office Action for U.S. Appl. No. 13/321,708, mailed Aug. 5, 2016, 30 pages.
Tian, J., et al., "Chitosan microspheres as candidate plasmid vaccine carrier for oral immunisation of Japanese flounder (*Paralichthys olivaceus*)," Dec. 15, 2008, pp. 220-229, vol. 126, Nos. 3-4, Veterinary Immunology and Immunopathology.
Kumar, S.R., et al., "Potential use of chitosan nanoparticles for oral delivery of DNA vaccine in Asian sea bass (*Lates calcarifer*) to protect from *Vibrio* (*Listonella*) *anguillarum*," Jul. 2008, pp. 47-56, vol. 25, Nos. 1-2, Fish & Shell Immunology.
Canandian Office Action dated Sep. 9, 2016 for Canadian Application No. 2756883, 4 pages.

\* cited by examiner

| Process loss of *L. rhamnosus* during drying of different culture types and at different freezing temperatures ||
| --- | --- |
| Culture Type | Log loss |
| Frozen culture | 0.91 |
| Dry culture | 0.44 |
|  |  |
| Freezing Temperature |  |
| +4°C | 0.73 |
| -80°C | 0.96 |
| -180°C | 0.9 |
| * the losses for freezing temperatures were evaluated on frozen bacterial cultures ||
| **Process losses were obtained after drying with no additional purging step. ||

FIG. 14

Shelf storage stability at 40°C and 43% RH and 30°C and 60% RH of commonly freeze dried *L. rhamnosus* sp. or after formulating in the composition and methods of the present invention.

Effect of compression in tablet press on viability and storage stability at 40°C and 43% RH of the probiotic L. rhamnosus stabilized and protected in the composition of the present invention.

STABILIZING COMPOSITION FOR BIOLOGICAL MATERIALS

CROSS REFERENCE TO RELATED APPLICATIONS

This application is a continuation in part of U.S. application Ser. No. 13/378,106, filed 29 Mar. 2012, which is the National Stage entry of International Application No. PCT/US11/22821, filed 28 Jan. 2011, which claims priority of U.S. Provisional Application No. 61/299,315, filed 28 Jan. 2010. This application is also a continuation in part of U.S. application Ser. No. 13/208,459, filed 12 Aug. 2011, which claims priority of U.S. Provisional Application No. 61/373,711 filed 13 Aug. 2010. This application further claims priority of U.S. Provisional Application No. 61/614,994, filed 23 Mar. 2012, U.S. Provisional Application No. 61/642,094, filed 3 May 2012, and U.S. Provisional Application No. 61/646,337, filed 13 May 2012. The content of all of the above applications is hereby incorporated by reference herein for all purposes.

BACKGROUND OF THE INVENTION

The preservation of the structure and function of biological materials during long-term storage at high temperature and humidity is of fundamental importance to the food, nutraceutical and pharmaceutical industries. Sensitive biological materials, such as proteins, enzymes, cells, bacteria and viruses must often be preserved for long-term storage for later use. Although many methods have been tried for stabilizing biological materials in storage, many are not suitable for sensitive bioactives, such as live or attenuated bacteria and viruses. For example, traditional freeze-drying combines the stresses due to both freezing and drying. The freezing step of this process can have undesirable effects, such as the denaturation of proteins and enzymes, and rupture of cells.

A need exists for a stabilizing composition that is useful for a wide range biological materials and that provides superior stabilization and preservation of biological materials over extended periods of time at elevated temperatures and varying degrees of humidity, such as can be encountered during shipping and storage of materials, while still retaining a significant amount of activity upon rehydration. A need also exists for stabilizing compositions that can be used in tableting applications without excessive loss of activity of biological materials, many of which are sensitive to the high pressures and temperatures encountered during tableting.

SUMMARY OF THE INVENTION

In one aspect, the invention provides a dry stabilizing composition for a bioactive material, including a carbohydrate component including between about 10% and 80% oligosaccharide, between about 5% and 30% disaccharide and between about 1% and 10% polysaccharide; and a protein component including between about 0.5% and 40% hydrolyzed animal or plant proteins; based on the total weight of the composition. The composition may be combined with a bioactive material.

In another aspect, the invention provides a method of producing the above composition combined with the bioactive material, including: (a) combining the bioactive material with at least the carbohydrate component and the protein component in an aqueous solvent to form a viscous slurry; (b) snap-freezing the slurry in liquid nitrogen to form solid frozen particles, beads, droplets or strings; (c) primary drying by water removal under vacuum of the product of step (b) while maintaining it at a temperature above its freezing temperature; and (d) secondary drying of the product of step (c) at maximum vacuum and a temperature of 20° C. or higher for a time sufficient to reduce the water activity to below 0.3 Aw.

In another aspect, the invention provides a tablet, pill or pellet made by compaction of a sensitive bioactive material embedded in a dry glassy and amorphous composition including one or more sugars and one or more hydrolyzed proteins, wherein the sugars include between about 10% and 60% and the hydrolyzed proteins include between about 1% and 40% based on the total dry weight of the composition.

In yet another aspect, the invention provides a method for producing the above-mentioned tablet, pill or pellet, including compacting the sensitive bioactive material embedded in the dry glassy and amorphous composition, wherein the dry glassy and amorphous composition is made by a process including: (a) combining a bioactive material with at least the one or more sugars and the one or more hydrolyzed proteins in an aqueous solvent to form a viscous slurry; (b) snap-freezing the slurry in liquid nitrogen to form solid frozen particles, beads, droplets or strings; (c) primary drying by water removal under vacuum of the product of step (b) while maintaining it at a temperature above its freezing temperature; and (d) secondary drying of the product of step (c) at maximum vacuum and temperature of 20° C. or higher for a time sufficient to reduce the water activity to below 0.3 Aw.

BRIEF DESCRIPTION OF THE DRAWINGS

FIG. 14. Process and drying losses of *L. rhamnosus* in compositions and drying methods of the invention.

DETAILED DESCRIPTION OF THE INVENTION

Definitions

Figure 1:
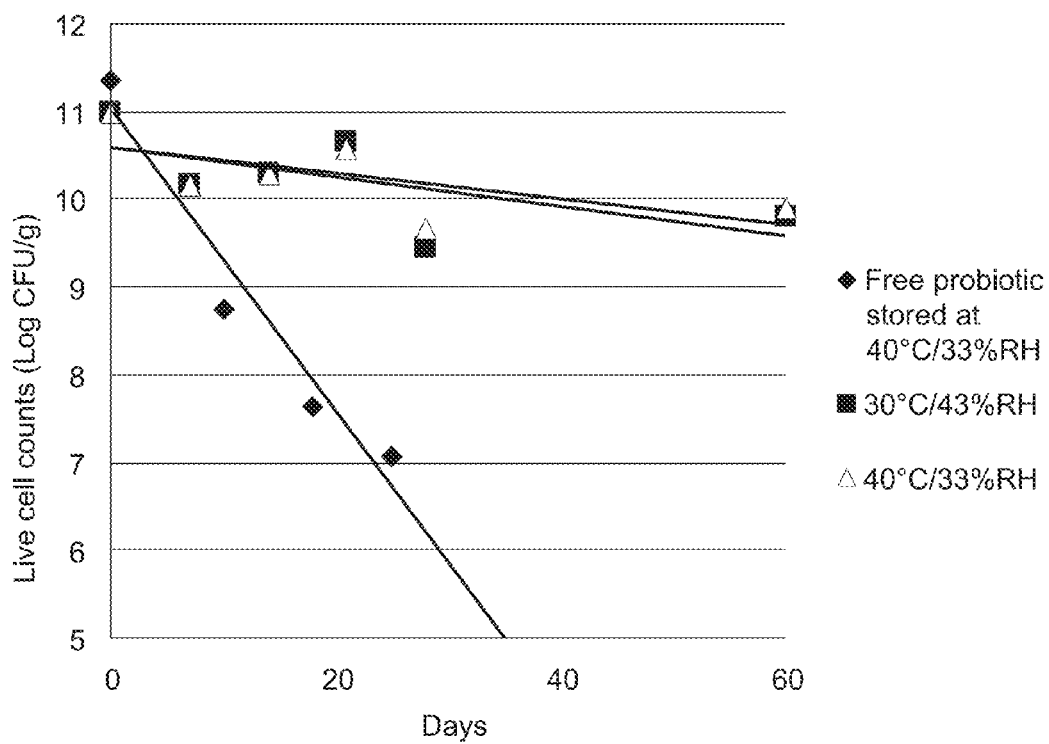
FIG. 1 shows acceleration stability of commercially available probiotic bacteria and probiotic bacteria in dry composition of the present invention.

It is to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a protein" includes singular protein or a combination of two or more proteins; reference to "enzyme", "bacteria", etc., includes singular or mixtures of several types, and the like.

In describing and claiming the present invention, the following terminology will be used in accordance with the definitions set out below.

"Bioactive ingredient," "bioactive material" and "biological material" all refer to microorganisms or ingredients that permit biological activity. Bioactive materials suitable for use with the present invention include, but are not limited to peptides, proteins, enzymes, hormones, nucleic acids, antibodies, drugs, vaccines, yeast, fungus, bacteria (probiotic or otherwise), soil microbes, viruses and/or cell suspensions.

"Biological composition" refers to preparations, which are in such a form as to permit the biological activity of the bioactive ingredients or agents to be unequivocally effective.

"Glass enhancer," "glass enhancing compound," and "glass forming agent" are used interchangeably herein to denote a chemical compound with the ability to form amorphous or glassy structure below a critical temperature, the glass transition temperature (Tg). During the formation of glassy structure, biological substances can become embedded within the glass structure. Glass enhancers suitable for use with the present invention include, but are not limited to, include salts of organic acids such as lactic acid, ascorbic acid, maleic acid, oxalic acid, malonic acid, malic acid, succinic acid, citric acid, gluconic acid, glutamic acid, and the like. Salts may include cations such as sodium, potassium, calcium, magnesium, phosphate and the like. Other useful glass enhancers include proteins, protein hydrolysates, polypeptides and amino acids. A combination of glass forming agents is also contemplated within a single composition. The process used to obtain a glassy structure for the purposes of this invention is generally a solvent sublimation and/or evaporation technique. Ideally, compounds that are GRAS compounds are preferred over those that are not GRAS.

"Sugars" refers to saccharides predominantly composed of carbon, hydrogen, and oxygen. Useful saccharides include reducing and non-reducing sugars and sugar alcohols and disaccharides. Two monosaccharides linked together form a disaccharide. The two monosaccharides used to form a disaccharide can be the same or different. Examples of disaccharides which can be used in the composition of the present invention include sucrose, trehalose, lactose, maltose, isomaltose. Sulfated disaccharides may also be used.

"Carbohydrates" or "polyhydroxy compound" refers to saccharides predominantly composed of carbon, hydrogen, and oxygen. A saccharide typically composed of a sugar backbone of repeating structural units linked in linear or non linear fashion, some of which contain positively or negatively charged chemical groups. The repeating units may range from two to several million. Useful saccharides include reducing and non reducing sugars and sugar alcohols, disaccharides, oligosaccharides, water soluble polysaccharides and derivatives thereof. Two monosaccharides linked together form a disaccharide. The two monosaccharides used to form a disaccharide can be the same or different. Examples of disaccharides which can be used in the carbohydrates mixture of the present invention include, sucrose, trehalose, lactose, maltose, isomaltose. Sulfated disaccharides may also be used. Small number of monosaccharides linked together (typically from three to twenty) form an oligosaccharide. The monosaccharides used to form an oligosaccharide can be the same or different components sugars. Examples of oligosaccharides suitable for use include, inulin, maltodextrins, dextrans, fructo-oligosaccharides (FOS), galacto-oligosaccharides (GOS), mannan-oligosaccharides (MOS) and combinations thereof. Large number of monosaccharides linked together (typically more than twenty) form a polysaccharide. The monosaccharides used to form a polysaccharide can be the same or different components sugars. Examples of polysaccharides suitable for use include, but are not limited to, methylcellulose, hydroxypropylcellulose, hydroxyethylcellulose, and hypromellose; soluble starches or starch fractions, xanthan gum, guar gum, pectins, carrageen, galactomannan, gellan gum, including any derivatives of these, cellulose acetate phthalate (CAP), carboxy-methyl-cellulose, sodium alginate, salts of alginic acid, hydroxyl propyl methyl cellulose (HPMC), gum acacia, locust bean gum, chitosan and chitosan derivatives, collagen, polyglycolic acid, starches and modified starches and cyclodextrins.

"Hydrolyzed protein" refers to protein that has been subjected to partial or full acid or enzymatic hydrolysis to yield a hydrolyzed protein having a molecular weight of from about 1 kDa to about 50 kDa. In some embodiments, referred to herein as "extensively hydrolyzed protein", at least 20% of the protein substrate is converted into peptides having molecular masses from 200 to 2000 dalton. The hydrolyzed protein has approximately the same amino acid composition as full protein and may be obtained from any number of commercial sources. Being hypoallergenic, hydrolyzed protein may advantageously be used in certain food for hyper sensitive consumers such as infants and elderly.

A "stable" formulation or composition is one in which the biologically active material therein essentially retains its physical stability, chemical stability, and/or biological activity upon storage. Stability can be measured at a selected temperature and humidity conditions for a selected time period. Trend analysis can be used to estimate an expected shelf life before a material has actually been in storage for that time period. For live bacteria, for example, stability is defined as the time it takes to lose 1 log of CFU/g dry formulation under predefined conditions of temperature, humidity and time period.

"Viability" with regard to bacteria, refers to the ability to form a colony (CFU or Colony Forming Unit) on a nutrient media appropriate for the growth of the bacteria. Viability, with regard to viruses, refers to the ability to infect and reproduce in a suitable host cell, resulting in the formation of a plaque on a lawn of host cells.

"Ambient" room temperatures or conditions are those at any given time in a given environment. Typically, ambient room temperature is 22-25° C., ambient atmospheric pressure, and ambient humidity are readily measured and will vary depending on the time of year, weather and climatic conditions, altitude, etc.

"Water activity" or "Aw" in the context of dried formulation compositions, refers to the availability of water and represents the energy status of the water in a system. It is defined as the vapor pressure of water above a sample divided by that of pure water at the same temperature. Pure distilled water has a water activity of exactly one, i.e., Aw=1.0.

"Relative Humidity" or "RH" in the context of storage stability refers to the amount of water vapor in the air at a given temperature. Relative humidity is usually less than that required to saturate the air and expressed in percent of saturation humidity.

"Dry" and variations thereof refer to a physical state that is dehydrated or anhydrous, i.e., substantially lacking liquid. Drying includes for example, spray drying, fluidized bed drying, lyophilization, and vacuum drying.

"Lyophilize" or freeze drying refers to the preparation of a composition in dry form by rapid freezing and dehydration in the frozen state (sometimes referred to as sublimation). Lyophilization takes place at a temperature which results in the crystallization of the sugars. This process may take place under vacuum sufficient to maintain frozen product, in some embodiments lower than about <2000 mTORR.

"Primary water removal" or "primary drying" step or "liquid drying", with regard to processes described herein, refers to the dehydration drying that takes place from the time of thawing the frozen particles to the point where secondary drying starts. Typically, the bulk of primary drying takes place by extensive evaporation, while the product temperature remained significantly lower than the temperatures of the heat source. This process may take place under vacuum sufficient to maintain thawed product, in some embodiments greater than about >2000 mTORR.

"Secondary drying", with regard to processes described herein, refers to a drying step that takes place at temperatures of the formulation near the temperature of the heat source. This process may take place under vacuum sufficient to reduce the water activity of a formulation, in some embodiments less than about <1000 mTORR. In a typical formulation drying process, a secondary drying step reduces the water activity of the formulation to an Aw of 0.3 or less.

The present invention includes compositions and drying methods for preserving sensitive bioactive materials, such as peptides, proteins, hormones, nucleic acids, antibodies, drugs vaccines, yeast, bacteria (probiotic or otherwise), viruses and/or cell suspensions, in storage.

The compositions and drying methods of the present invention solve the problem of providing a cost effective and industrially scalable dry formulations containing sensitive bioactive materials, such as peptides, proteins, hormones, nucleic acids, antibodies, drugs, vaccines, yeast, bacteria, viruses and/or cell suspensions, with a significantly extended lifetime in the dry state. The invention provides a preservation composition and a drying method comprising a biological material surrounded by amorphous glassy structure of highly soluble compounds. The drying process comprises: mixing the biological material and the composition in a liquid slurry, snap-freezing said composition slurry in liquid nitrogen to form droplets, strings or beads, followed by drying the bioactive material in a sugar glass formation by evaporating the moisture under a regimen of reduced pressure while supplying heat to the composition.

The present invention is based on the remarkable discovery that biological materials can be protected in glassy structure while retaining substantial activity. When the biological material is combined with the composition mixture and dried according to the present invention a superior stability was achieved during extended time exposure to harsh temperature and humidity conditions. The present invention includes compositions containing a biological material, a mixture of soluble carbohydrates and glass enhancing carboxylic acid salts. The compositions of the invention are inherently different in their physical structure and function from non-viscous or concentrated sugary compositions that were simply dried under a typical freeze drying process. For example, U.S. Pat. No. 6,919,172 discloses an aerosolized powder composition for pulmonary administration, which contains a mixture of various carbohydrates and sodium citrate. However, the composition described in the patent lacks the additional proteinous compound that is essential for added stability and for the formation of a desirable physical structure during drying of solutions having high concentration of sugars. The described composition in this patent also lacks viscosity or hydrogel structure, which allows an efficient drying of thawed or unfrozen solution for enhanced glass formation. In contrast, the composition and drying process of the present invention overcomes all these issues while achieving a superior stability of the biological material. The prior art also lacks the additional carboxylic component that act in synergism with the hydrolyzed proteins to protect and stabilize the biological material.

Enhanced glassy structure was usually achieved in the prior art by foaming or boiling the solution under vacuum to facilitate effective drying. The foaming step generally resulted in an extensive boiling and eruption of the solution that is an unavoidable consequence of the drying of unfrozen solution, and as a result, only a very low loading capacity of solution in a vial or a vessel can be achieved (see for example U.S. Pat. No. 6,534,087, in which the thickness of the final foamed product is less than 2 mm). The compositions and drying methods of the present invention avoid boiling and foaming of the formulation thereby enabling much higher loading of material per drying area and, as a result, can be easily scaled up to the production of large quantities of material without the use of specifically designed vessels and trays or equipment.

A wide range of biological materials can be used with the inventive composition to form an aqueous preservation medium according to the invention. This preservation medium can then be subjected to the drying processes of the present invention to make a stable dry powder of biological material. These biological materials, include, without limitation: enzymes, such as pancreatic enzymes, lipases, amylases, protease, phitase, lactate dehydrogenase; proteins, such as insulin; vaccines; viruses, such as adenovirus; cells, including prokaryotic cells (including bacteria and fungi) and eukaryotic cells, other biological materials, including drugs, nucleic acids, peptides, hormones, vitamins, carotenoids, minerals, antibiotics, microbiocides, fungicides, herbicides, insecticides, spermicides, antibodies and lipid vesicles.

Figure 15:
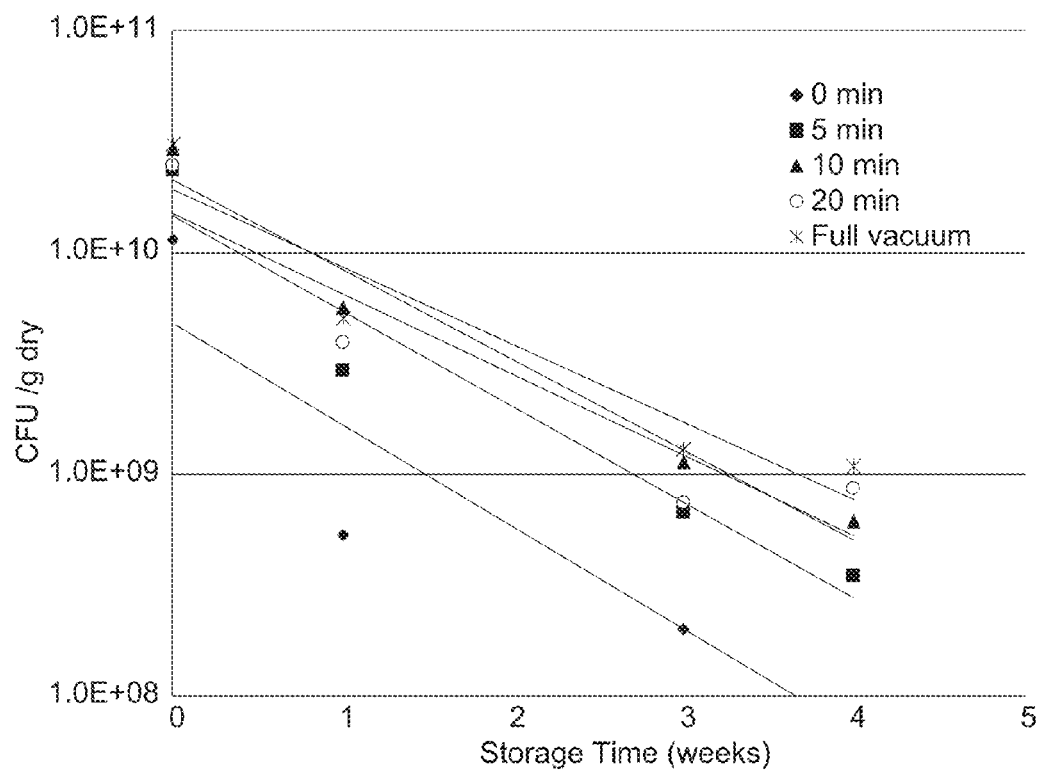
FIG. 15. Stability trends of dry probiotic bacteria, *L. rhamnosus* composition in storage at 40° C. and 33% relative humidity.

Probiotic bacteria have been shown to benefit particularly from the compositions and drying methods of the present invention. The stable dry probiotic powder is prepared according to the compositions and methods of the invention including mixing fresh, frozen or dry cultures of probiotic bacteria with a mixture of carbohydrates and glass enhancing compounds, snap-freezing the viscous formulation in liquid nitrogen to form frozen solid droplets, strings or beads, and drying by initially applying sufficient vacuum to increase the formulation temperature above the freezing temperature and supplying a heat source of 20° C. and higher to facilitate primary water removal. Maintaining the temperature of the formulation above the freezing point can be accomplished by adjusting the vacuum and by conduction of heat to the formulation. To complete the drying process and further reduce the water activity of the formulation below Aw of 0.3 or lower, a secondary drying step is applied at maximum vacuum and at elevated temperature up to 70° C. Such a composition can remain stable in storage conditions of 40° C. and 33% RH for 30 days or more, as shown in FIG. 15.

Live microorganisms such as probiotic bacteria in compressed tablets have been shown to benefit particularly from the compositions and drying methods of the present invention. The stable dry biological powder is prepared according to the compositions and methods of the invention including mixing fresh, frozen or dry cultures of single cell organisms with a mixture of sugars, hydrolyzed proteins and an antioxidant and potentially including additional amounts of polysaccharides and oligosaccharides and glass enhancing compounds, snap-freezing the viscous formulation in liquid nitrogen to form frozen solid droplets, strings or beads, evaporating the water by initially applying sufficient vacuum to increase the formulation temperature above its freezing temperature and supplying a heat source of 20° C. and higher to facilitate primary water removal. Maintaining the temperature of the formulation above the freezing point can be accomplished by adjusting the vacuum and by conducting or radiating heat to the formulation. To complete the drying process and further reduce the water activity of the formulation below Aw of 0.3 or lower, a secondary drying step is applied at maximum vacuum and at elevated temperature up to 70° C.

Compositions of the Invention

In some embodiments, the formulation comprises a carbohydrate mixture of di-, oligo- and poly-saccharides, in which the bioactive material is embedded. Examples of a suitable polysaccharide, include but is not limited to, cellulose acetate phthalate (CAP), carboxy-methyl-cellulose, pectin, sodium alginate, salts of alginic acid, hydroxylpropyl methyl cellulose (HPMC), methyl cellulose, carrageenan, gellan gum, guar gum, gum acacia, xanthan gum, locust bean gum, chitosan and chitosan derivatives, collagen, polyglycolic acid, starches and modified starches. Examples of a suitable oligosaccharide, include but is not limited to, cyclodextrins, fructans, inulin, FOS, maltodextrins, dextrans, etc.; and combinations thereof. Examples of a suitable disaccharide, include but are not limited to, lactose, trehalose, sucrose, etc. In one particular embodiment, a suitable exemplary polysaccharide is sodium alginate or gellan gum. In another embodiments, the formulation comprises, in percent by weight of total dry matter, 0.1-20% of sodium alginate.

In some embodiments, the carbohydrate mixture comprises, in percent by weight of total dry matter, 0.1-10% polysaccharides, 1-10% oligosaccharides and 10-90% disaccharides. In an additional embodiment, the carbohydrates mixture comprises di-, oligo- and poly-saccharides in a weight ratio of 10:0.1-4:0.1-2, or wherein the weight ratio of disaccharides/oligosaccharides/polysaccharides is from about 10:0.2:0.1 to about 10:2:1.

In some embodiments the disaccharide fraction in the carbohydrate mixture includes various sugars and sugar alcohols. Suitable disaccharides are ones that do not crystallize and/or damage or destabilize the biologically active material in the formulation at freezing temperatures (e.g., lower than −20° C.) and during water removal. For example, bioactive material can be dried in the presence of glass forming sugars such as sucrose, lactose or trehalose to promote retention of molecular structure throughout the drying process and impart structural rigidity to the amorphous matrix in the dry state. A suitable disaccharide would effectively replace water of hydration lost during drying, to prevent damage to cell membranes and denaturation of enzymes (see review by Crowe et al., 1998). Other functions of the disaccharide in the composition can include protecting the bioactive material from exposure to damaging light, oxygen, oxidative agents and moisture. A suitable disaccharide must readily dissolve in a solution. Trehalose is a particularly attractive protectant because it is a non-reducing disaccharide found in plants and living organisms (e.g., bacteria, fungi and invertebrates such as insects and nematodes) that remain in a state of dormancy during periods of drought. In some cases, it can be beneficial to include two or more different disaccharides such as a mixture of trehalose and sucrose to inhibit the formation of crystals, to enhance the stability of the dried bioactive material formulation in storage conditions for extended time periods and to reduce costs.

In some embodiments the oligosaccharide fraction in the carbohydrate mixture includes inulin, maltodextrins, dextrans, fructo-oligosaccharides (FOS), galacto-oligosaccharides (GOS), mannan-oligosaccharides (MOS) and combinations thereof. The oligosaccharides mitigate several problems associated with the use of trehalose alone as a protectant for a variety of preserved biological materials.

Although very effective in protecting the biological material during dehydration and rehydration, trehalose alone as a stabilizer does not provide desirable storage stability for extended periods of time, especially at high temperatures and/or humid environments. This problem was resolved in the present invention with the addition of oligosaccharides, for example inulin, to the carbohydrate mixture.

A suitable exemplary mass ratio of the saccharides in the carbohydrates mixture is 10:0.1-10:0.1-2 disaccharides/oligosaccharides/polysaccharides and in some embodiments, wherein the weight ratio of disaccharides/oligosaccharides/polysaccharides is from about 10:0.2:0.1 to about 5:10:1. In some embodiments, the carbohydrate mixture comprises, in percent by weight of total dry matter, 10-90% disaccharides, 1-10% oligosaccharides and 0.1-10% polysaccharides. In other embodiments, the carbohydrates mixture comprises in percent by weight of total dry matter, 10-50% disaccharides, 10-80% oligosaccharides and 0.1-10% polysaccharides.

In a particular embodiment, the formulation comprises a mixture of oligosaccharides. The oligosaccharides mixture mitigates several problems associated with the use of a single oligosaccharide alone as a glass enhancing material in the composition. Although very effective in elevating the glass transition temperature oligosaccharides tend to rapidly crystallize and precipitate and thereby fragmenting the glassy amorphous structure, especially at high temperatures and/or humid environments. This problem was resolved in the present invention with the addition of a mixture of oligosaccharides instead of a single type of oligosaccharide, in some embodiments a mixture of fructans and low DE dextrins. In some embodiments, the carbohydrate mixture comprises, in percent by weight of total dry matter, 5-40% fructans and 5-40% low DE dextrins.

One suitable composition comprises from about 0.5% to about 90% of a carbohydrate component including at least a di-, oligo- and poly-saccharide and a protein component comprising about 0.5% to about 40% of a hydrolyzed protein. In some embodiments, the composition comprises about 30% to about 70% of carbohydrate component and about 10% to about 40% of a glass enhancer component such as a protein hydrolyzed protein and carboxylic acid, wherein the carbohydrate component comprises about 10% to 90% or from about 40% to 80% of a disaccharide; about 1% to about 10% or from about 5% to 10% of an oligosaccharide; and about 0.1 to about 10% or from about 5% to about 10% of a polysaccharide. The composition further comprises a salt of an organic acid which is considered to be another glass enhancer component and comprises between about 0.5% and 20% carboxylic acid, based on the total weight of the composition.

In an additional embodiment, the composition comprises a mixture of sodium alginate and oligosaccharides in a weight ratio of 1:1-10, or 1:1-5, of sodium alginate/oligosaccharides.

In yet another embodiment of the present invention, composition is cross-linked with divalent metals ions to form a firm hydrogel. In some embodiments, the cross-linked hydrogel formulation is formed by atomizing or extruding the slurry in a bath containing divalent metal ions solution or by adding divalent metal ions directly into the slurry and allowing the formulation to harden and form a hydrogel. The hydrogel formulation is then flash frozen and dried according to the drying methods of the invention.

In other embodiments, the composition comprises significant amounts of glass enhancing compounds including salts of organic acids such as lactic acid, ascorbic acid, maleic acid, oxalic acid, malonic acid, malic acid, succinic acid, citric acid, gluconic acid, glutamic acid, and the like. Salts may include cations such as sodium, potassium, calcium, magnesium, and the like. Examples include sodium citrate, sodium lactate, sodium maleate, magnesium gluconate, sodium ascorbate, and the like. Salts having high glass transition temperature (Tg) and high solubility are preferred. Exemplary organic acids include citric acid and its salts (e.g., sodium or potassium citrate, trisodium citrate dehydrate) and ascorbic acid and its salts (e.g., sodium ascorbate, potassium ascorbate, magnesium ascorbate). For example, in some embodiments the composition of the invention includes a carbohydrates mixture of di-, oligo- and polysaccharides and ions of organic acid such as citric acid and/or ascorbic acid.

The amount of glass enhancers used in the composition will vary depending on the overall composition and its intended drying storage conditions. Generally, the amount of the glass enhancing compound in the composition is higher than two (2) percent by weight of total dry matter while the pH of the solution or dispersion is maintained slightly alkali (pH 7-7.5). Without being bound by theory, it is believed that the function of the glass enhancing compound at relatively high content as described herein is not only to contribute to the desirable amorphous and rigid glassy structure of the resulting dry composition, but also to protect the bioactive material from exposure to damaging light, oxygen, oxidative agents and moisture. A suitable exemplary composition comprises, in percent by weight of total dry matter, 1-20% or about 2-10% of glass enhancing compound by weight of total dry matter.

Other suitable glass enhancers that are included in the composition to further increase its stability include proteins, protein hydrolysates, polypeptides and amino acids. These include gelatine, albumin, whey protein, soy protein, casein, caseinate, immunoglobulins, soy protein, pea protein, cottonseed protein or other food and dairy or vegetable proteins and/or their hydrolysates, or any other hydrolyzed protein. Examples of polyamino acids include polyalanine, polyarginine, polyglycine, polyglutamic acid and the like. Useful amino acids include lysine, glycine, alanine, arginine or histidine, as well as hydrophobic amino acids (tryptophan, tyrosine, leucine, phenylalanine, etc.) and a methylamine such as betaine.

In some embodiments, casein or pea protein or hydrolyzed casein or hydrolyzed pea proteins, are used. In some embodiments the hydrolyzed proteins fraction in the composition mixture includes partially hydrolyzed or extensively hydrolyzed proteins, polypeptides and amino acids. As used herein, the extensively hydrolyzed proteins are those obtained by extensive enzymatic hydrolysis through the use of proteases for the modification (breakdown) of proteins. In some embodiments, hydrolyzed animal or vegetable proteins such as casein, whey, soy, or pea proteins, or extensively hydrolyzed casein or pea proteins. Some embodiments employ extensively hydrolyzed proteins having over 80% short chain peptides with a molecular weight from about 1 kDa to about 50 kDa and at least 20% of the protein substrate is converted into peptides having molecular masses from 200 to 2000 dalton. Without being bound by theory, it is believed that a mixture resulting from a sugar and extensively hydrolyzed protein as described herein allows for faster drying and contributes to the desirable amorphous and rigid glassy structure of the resulting dry composition. An enzyme-hydrolyzed protein can be prepared by methods known to those skilled in the art or can be obtained from a commercial source. A suitable exemplary composition comprises, in percent by weight of total dry matter, 5-40% extensively hydrolyzed proteins.

A suitable exemplary total amount of proteins, hydrolyzed protein or extensively hydrolyzed proteins and amino acids in the dry composition is from about 1% to about 40%, or about 5% to about 40%, or about 10% to about 30% of the total mass of dry mixture.

It should be noted that the proper amount of the glass enhancers in the composition may depends on the desired characteristics of the dry composition. For example, a composition containing carbohydrate mixture and protein or protein hydrolysates can be used to enhance the chemical stability of a biological material while being stored under mild temperature and relative humidity, such as 25° C. and 25% RH. The determination of the proper amount of glass enhancers, and particularly the relative ratio between the disaccharides and oligosaccharides, should be made according to the desired storage conditions. For example, a composition containing high ratio of disaccharide/oligosaccharides can be used to enhance the chemical stability of a biological material while being stored under mild temperature and relative humidity, such as 25° C. and 25% RH. A composition containing low ratio of disaccharide/oligosaccharides can be used to enhance the chemical stability of a biological material while being stored under high temperature and relative humidity, such as 30° C. and 40% RH or above.

Ascorbic acid ions may be preferred in some embodiments as glass enhancers to obtain added benefit of stabilizing at higher temperature and humidity exposure. Alternatively, in some embodiments a combination of citrate and/or ascorbate ions with another glass enhancer, such as protein or protein hydrolysate, is more preferred.

In some embodiments the formulation comprises a mixture of sugars and hydrolyzed proteins, in which the bioactive material is embedded. Examples of suitable sugars include, but are not limited to, disaccharides such as lactose, trehalose, sucrose and a mixture thereof. Examples of suitable hydrolyzed proteins include, but are not limited to, extensively hydrolyzed gelatine, albumin, whey protein, soy protein, casein, caseinate, immunoglobulins, soy protein, pea protein, cottonseed protein or any other extensively hydrolyzed proteins from dairy, animal or plant origin and a mixture thereof. A suitable exemplary total amount of sugars in the dry composition is from about 10% to about 80% of the total mass of dry mixture, or from about 10% to about 60% of the dry mass.

In one exemplary embodiment, the glass forming agent comprises a mixture of a disaccharide and a hydrolyzed protein. In a particular embodiment, a suitable exemplary glass forming agent is a mixture of trehalose and hydrolyzed protein. In some embodiments, the formulation comprises, in percent by weight of total dry matter, 10-90%, of trehalose and 0.1-30% hydrolyzed protein, or 20-80% of trehalose and 0.1-20% hydrolyzed protein, or 40-80% of trehalose and 0.1-20% hydrolyzed protein.

Ideally, compounds that are Generally Recognized As Safe (GRAS) compounds are preferred over those that are not GRAS. Others include an excipient salt such as magnesium sulfate; a polyol such as trihydric or higher sugar alcohols, (e.g. glycerin, erythritol, glycerol, arabitol, xylitol, sorbitol, and mannitol); propylene glycol; polyethylene glycol; pluronics; surfactants; and combinations thereof.

In some embodiments, the biological material comprises live bacteria (e.g., probiotic bacteria). Examples of suitable microorganisms include, but are not limited to, yeasts such as *Saccharomyces*, *Debaromyces*, *Candida*, *Pichia* and *Torulopsis*, moulds such as *Aspergillus*, *Rhizopus*, *Mucor*, *Penicillium* and *Torulopsis* and bacteria such as the genera *Bifidobacterium*, *Clostridium*, *Fusobacterium*, *Melissococcus*, *Propionibacterium*, *Streptococcus*, *Enterococcus*, *Lactococcus*, *Kocuriaw*, *Staphylococcus*, *Peptostrepococcus*, *Bacillus*, *Pediococcus*, *Micrococcus*, *Leuconostoc*, *Weissella*, *Aerococcus*, *Oenococcus* and *Lactobacillus*. Specific examples of suitable probiotic microorganisms would be represented by the following species and include all culture biotypes within those species: *Aspergillus niger, A. oryzae, Bacillus coagulans, B. lentus, B. licheniformis, B. mesentericus, B. pumilus, B. subtilis, B. natto, Bacteroides amylophilus, Bac. capillosus, Bac. ruminocola, Bac. suis, Bifidobacterium adolescentis, B. animalis, B. breve, B. bifidum, B. infantis, B. lactis, B. longum, B. pseudolongum, B. thermophilum, Candida pintolepesii, Clostridium butyricum, Enterococcus cremoris, E. diacetylactis, E faecium, E. intermedius, E. lactis, E. muntdi, E. thermophilus, Escherichia coli, Kluyveromyces fragilis, Lactobacillus acidophilus, L. alimentarius, L. amylovorus, L. crispatus, L. brevis, L. case 4 L. curvatus, L. cellobiosus, L. delbrueckii ss. bulgaricus, L farciminis, L. fermentum, L. gasseri, L. helveticus, L. lactis, L. plantarum, L. johnsonii, L. reuteri, L. rhamnosus, L. sakei, L. salivarius, Leuconostoc mesenteroides, P. cereviseae (damnosus), Pediococcus acidilactici, P. pentosaceus, Propionibacterium freudenreichii, Prop. shermanii, Saccharomyces cereviseae, Staphylococcus carnosus, Staph. xylosus, Streptococcus infantarius, Strep. salivarius ss. thermophilus, Strep. Thermophilus* and *Strep. lactis*.

Methods of Making the Compositions

One suitable mixing process of the biological material and the composition is by adding the total dry composition mixture in a concentrate culture or media solution containing biological material. The weight mass of the biological material in the culture media is typically between about 5% and 30% w/v, or between about 10% and 20% w/v. The added weight mass of the composition mixture in the culture media is typically between about 10% and about 60%, or between about 20% and 40%. The final solid content in the mixed slurry is from about 20% to about 60% and more specifically from about 30% to about 50%. In some embodiments, the solution is mixed at room temperature or slightly warmed to assist in solubilizing the materials in the viscous solution (e.g., from 20° C. to 40° C.). In a variation of the present invention, the total amount of the carbohydrates mixture in the formulation is adjusted to achieve a desired formulation viscosity and density that allowed an efficient drying while avoiding rubbery formation or excessive foaming that may occurs during the drying step. A suitable exemplary slurry viscosity is from about 1,000 cP to about 500,000 cP, or from about 5,000 cP to about 300,000 cP. A desired viscosity and density of the final slurry can be achieved by any means known in the art, for example, slightly adjusting the amount of the polysaccharides in the carbohydrates mixture or by degassing or injecting gas such as air, nitrogen, carbon dioxide, argon etc.

The biological material slurry of the present invention is typically snap-frozen to between −30° C. to −180° C., or the formulation is snap-frozen in liquid nitrogen by atomizing, dripping or injecting into liquid nitrogen bath. Collecting the particles, beads, strings or droplets from the liquid nitrogen bath and drying in a freeze drier or vacuum drier, or alternatively storing them in a deep freezer (between −30° C. and −80° C.) for later use in a frozen form or for later drying, e.g., by spray drying.

In general, the drying process techniques that are useful include spray drying; or evaporative drying of a non-frozen solution in a vacuum oven or centrifugal evaporator at temperatures above the freezing temperature of the slurry (−20 to 50° C.), followed by milling to desirable particle size. The resultant powder particles are glassy with a majority of the glassy materials coating the biological material. The advantage of coating the biological material with glassy materials is to increase physical stability of the product and reduction of deleterious intermolecular reactions within the particle. In a suitable exemplary embodiment, the frozen particles is loaded on trays and immediately transferred to a vacuum drying chamber where the drying process proceeds in three major steps including: (1) An optional, short purging and structure stabilizing step of the frozen particles under a vacuum pressure of less than <2000 mTORR, (2) Primary drying step under vacuum of more than >2000 mTORR and at a temperature above the freezing point of the slurry, and (3) Secondary and final drying step of the glassy amorphous material under full vacuum pressure and elevated temperature for a time sufficient to reduce the water activity of the dried formulation to 0.3 Aw or less.

In one particular embodiment of the present invention, the dried formulation is granulated with a mixture of molten fats to obtain enhanced preservation in short periods of exposure to extreme temperature and humidity conditions.

The dried and stable biological composition can be used directly as a flake, or ground into a powder and sieved to an average particle size from about 10 μm to about 1000 μm. The formulation can be administrated directly to an animal, including man, as a concentrated powder, as a reconstituted liquid, (e.g., a beverage), or it can be incorporated either in flake or powder form into an existing food or feed or agricultural product.

In some embodiments, compositions for the preparation of stable frozen or dry powder of biological materials according to the invention include a carbohydrate mixture and glass enhancer. Such materials, when mixed with the bioactive material, form beads strings or droplets in liquid nitrogen and can be efficiently dried in an amorphous glassy structure according to methods of the invention and to provide large quantities of stable dry compositions for storage and administration of said bioactive material. (See FIGS. 7 and 8 for visual and microscopic observations and water activity (Aw) of different formulations after drying). The carbohydrates mixture provides structural stability to the formulation in high temperature and humidity such as above 30° C. and 40% RH. and/or physical and chemical protective benefits to the bioactive materials and prevents or reduces the adverse effects upon reconstitution or rehydration.

The polysaccharide fraction in the carbohydrate mixture can provide thickening viscosity to the formulation and better control over the formulation density properties under vacuum and increased structural strength to the dried formulation compositions of the invention. (See FIG. 8—Pictures 4, 4b, 4c for the glassy structure and dryness of that particular formulation). Suitable polysaccharides, particularly for live organisms, are water soluble gums, because of their distinctive characteristic to form viscous gel at mild temperatures. Gums at certain concentration were also found to effectively stabilize the formulation structure under vacuum, by providing appropriate viscosity and density to the formulation and allowing an effective drying of the formulation during the primary water removal step at a particular viscosity. Certain gums can also form hydrogels by cross-linking with divalent or multivalent cations (e.g., alginates, pectins, chitosan) or by temperature or pH changes (e.g., gelatins, CMC, CAP, gellan gum). Hydrogeled solutions would prevent problems associated with vacuum drying of unfrozen solutions. Gums at certain concentration were also found to effectively stabilize the formulation and facilitate the formation of an amorphous glassy structure and enhance drying profile under vacuum (see FIG. 7—pictures 3a, 3b, 3c, 4, and FIGS. 8-4c and FIG. 13).

Figure 7:
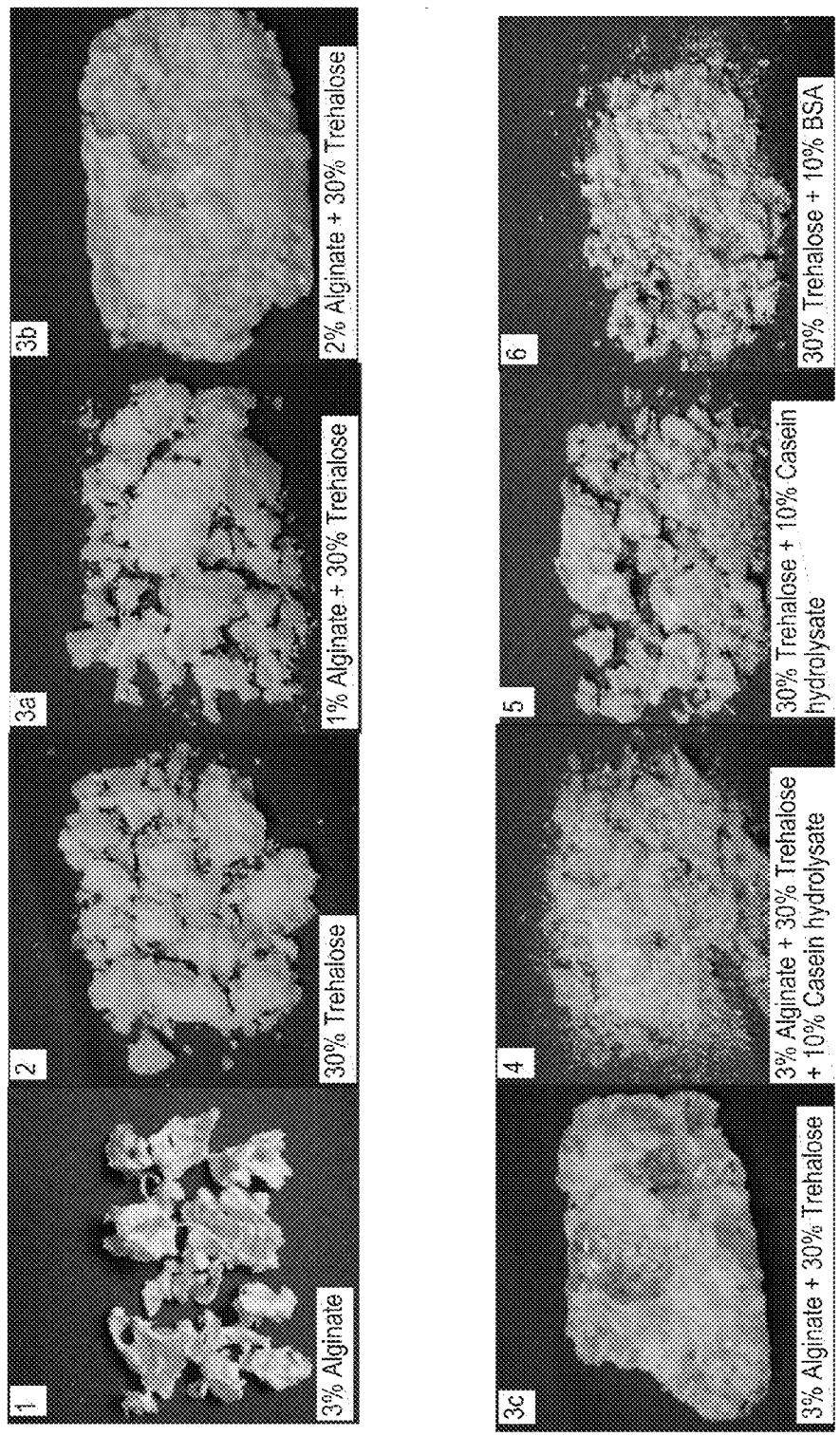
FIGS. 7 and 8. Visual and microscopic observations of different dried compositions containing various matrices and glass forming agents as frozen solid bead according to the method of the present invention.
Figure 8:
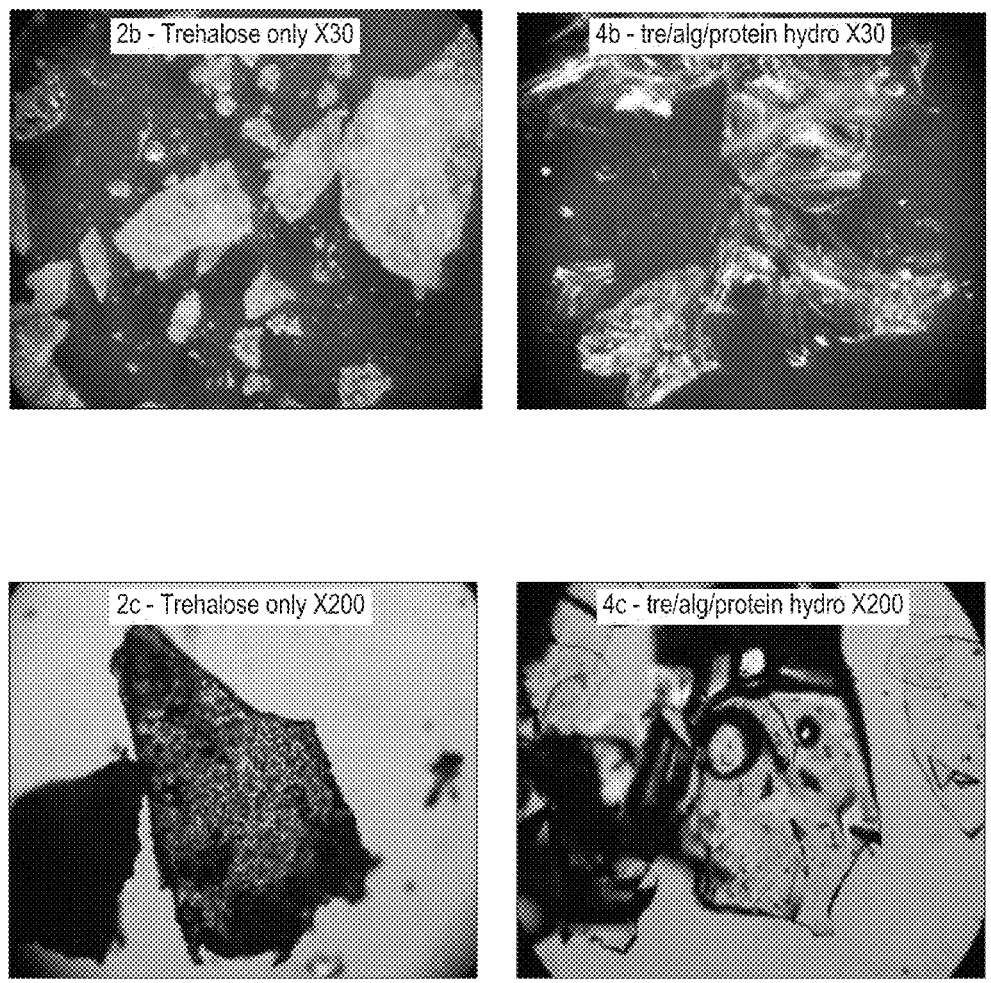
Figure 9:
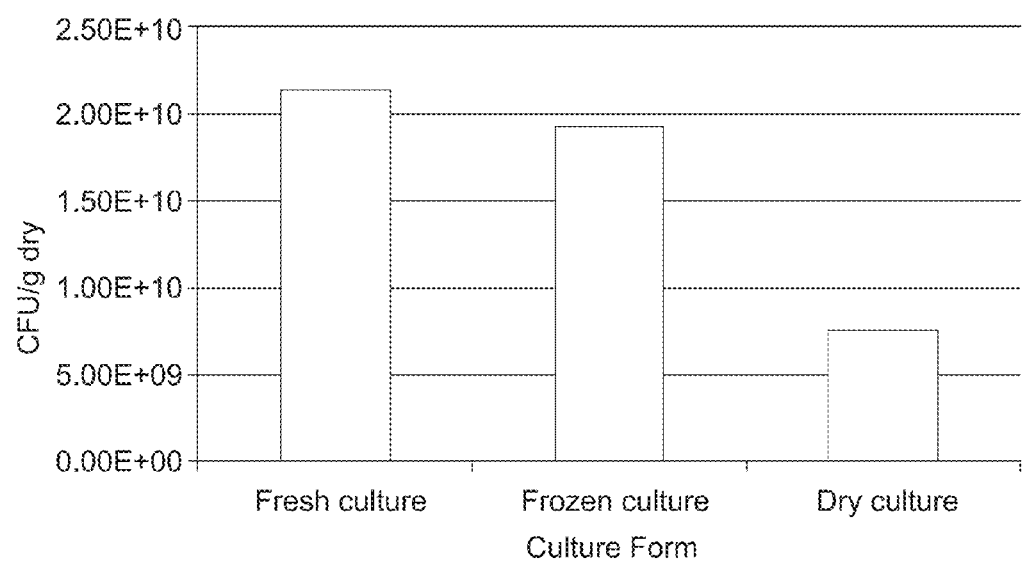
FIG. 9. The effect of *L. rhamnosus* culture form as fresh, frozen beads or dry powder cultures on its initial CFU counts in a dry composition.

Notably by viewing the pictures of FIG. 7 in combination with the results set forth below in Table 1, it is evident that samples 3b, 3c, 4, 5, and 6 were all dried sufficiently to provide some porosity in the amorphous glassy structures.

TABLE 1

Visual Inspection of the Various Dry Compositions

|  | 1 | 2 | 3a | 3b | 3c | 4 | 5 | 6 |
|---|---|---|---|---|---|---|---|---|
| Dryness | Not Dry | Not Dry | Not Dry | Dry | Dry | Dry | Dry | Dry |
| Porousness | None | None | None | Present | Present | Present | None | Partial |
| Aw | 0.847 | 0.923 | 0.916 | 0.216 | 0.183 | 0.376 | 0.171 | 0.112 |
| Glass Structure | None | None | None | Partial | Partial | Present | Partial | Partial |

For example, a dry form of bioactive material can be formulated into a solution or suspension containing the composition powder mixture. The composition mixture can be dissolved into a warm aqueous solution with low shear agitation before cooling and mixing with the bioactive material. The bioactive material, such as cultured virus or bacterium, can be concentrated and separated from the culture media by centrifugation or filtration before re-suspension into the formulation. Alternatively, the totality or a portion of the water in the formulation is provided in the liquid of the concentrated biological material. The suspension is maintained at a temperature slightly above room temperature and the dry composition powder mixture is slowly added to the warm (25° C. to 40° C.) suspension containing the biological material. The suspension is gently agitated in a planetary mixer until all components are fully dispersed or dissolved and uniform slurry is obtained.

The viscous slurry can be then cross-linked to form a hydrogel (depending on the polysaccharide properties) by adding metal ions or changing the temperature or pH of the slurry and then dried according to the drying methods of the invention. Alternatively, the slurry can be snap-frozen by atomizing through a nozzle, dripping or injecting in dry ice or liquid nitrogen bath to form small particles or solid droplets strings or beads. The frozen solid particles can be stored in a deep freezer between −30° C. and −80° C. for later use as a stable frozen product or until drying. A suitable exemplary drying method is vacuum drying where the product temperature is maintained slightly above its freezing temperature. The frozen droplets or beads are placed on trays at a loading capacity from about 0.1 kg/sq ft to about 1.5 kg/sq ft and dried according to the method of the invention. In some embodiments, the drying process is initiated by a short purging step, which allows the product acclimation to initial temperature and structure of the frozen particles to relax and stabilize and excess air degassed. Typically, the purging step takes between 1 and 60 minutes depending on the product viscosity and tray loading. The beads or particles should remain in a solid frozen form during the entire purging step. The product temperature is then brought to above its freezing temperature and primary water removal step followed until all free water is evaporated from the product. Once the formulation temperature reached the desired temperature, heat is adjusted to maintain that temperature and the primary liquid drying step by evaporation is progressed. At this step the formulation is already thawed and accelerated water evaporation take place without any boiling or foaming. The drying process is completed with an additional secondary drying phase at maximum vacuum and elevated temperature.

Typical methods in the prior art involve extensive foaming and/or splattering and violent boiling that can be damaging to sensitive biologicals and cause difficulties for industrial scale up at high loading capacity (see for example U.S. Pat. No. 6,534,087, where the applied vacuum pressure result in violent boiling and foaming). However, the current compositions and methods avoid boiling or foaming of the formulation while achieving a significantly faster drying rate and enabling a high loading capacity of the formulation. Additionally, a complete and efficient degassing of viscous liquid slurries is difficult and may require an extended period of time. These obstacles were all resolved in the present invention by using a suitable composition that allows an effective primary water removal while a glassy structure is formed without boiling and excessive foaming. The loading of solid frozen particles on a tray as oppose to slurry or viscous syrup allows much higher loading capacity per drying area on trays than was afforded according to the prior art.

In one suitable example of the present invention, the biological material is a live concentrate probiotic bacteria culture. A powder composition mixture in some embodiments contains 1-4% sodium alginate or gellan gum, 50-75% trehalose, 1-10% inulin or FOS, 10-20% protein hydrolysates, such as casein, whey, pea, soy or cottonseed hydrolysates and 1-10% sodium citrate or sodium ascorbate. The probiotic culture can be fresh, frozen or already dried in a form of dry powder.

In another suitable example of the present invention, the biological material is a live concentrate microorganism culture. A powder composition mixture is prepared by mixing 1-4% sodium alginate or gellan gum, 5-30% trehalose, 5-40% inulin, 5-40% low DE maltodextrin, 10-30% extensively hydrolyzed protein, such as casein, whey, pea, soy or cottonseed protein. Additional 0.1-10% glass enhancers such as sodium citrate, sodium glutamate or sodium ascorbate may also included in the composition, as an option. The microorganism or spore culture can be fresh, frozen or already dried in a form of dry powder.

The composition mixture is added to the concentrated probiotic culture media to bring the solid content of the solution mixture to 40-60% (w/w) and the pH adjusted to 6.5-7.5 with phosphate or citrate ions. The solution is mixed at a temperature slightly above the room temperature (typically between 25° C.-37° C.) until all the components are completely dissolved. The viscous slurry is dripped in liquid nitrogen to form small droplets or beads which are then removed from the liquid nitrogen, packed in bags and stored in a deep freezer at −80° C. until drying.

A typical drying method of live probiotic bacteria includes spreading the solid frozen beads on trays in a uniform layer at a loading capacity between 100-1500 g/sq ft, and the trays are immediately placed in a freeze drier. Vacuum is then applied at about 1000 mTORR or lower and depending on the freeze drier size and type of heat source, the shelf temperature adjusted to maintain the particles at about −20 to about −30° C. The solid frozen beads are allowed to purge for about 1 to about 60 minutes and vacuum adjusted to between 2000 and 10,000 mTORR and heat transfer increased to raise the formulation temperature to between −20° C. and 0° C., or between −10° C. and 0° C., typically about −10° C. These temperature and vacuum pressure conditions are maintained during the primary water removal step which may last from a few hours and up to 24 hours depending on the tray loading. At some point during the primary drying process, the rate of evaporation of solvent slows and the formulation temperature begins to increase due to excess supply of heat in the drying chamber. This point indicates the end of the primary drying step in this invention. As solvent is driven out from the formulation, the glass forming compounds in the solution become concentrated and thicker until it stops flowing as a liquid and form an amorphous and/or stable glassy structure.

A secondary drying step is then followed at maximum vacuum and formulation temperature between 30° C. and 50° C. The purpose of the secondary drying step is to remove the remaining entrapped or bound moisture and provide a composition that is stable in storage for an extended period of time at ambient temperatures. The secondary drying step may last several hours and its ending point is when the formulation is completely dry and its water activity lower than 0.3 Aw.

The drying methods of the invention result in a biologically active material that is encased within an amorphous glassy structure, thereby preventing the unfolding or denaturation of proteins and significantly slowing molecular interactions or cross-reactivity, due to greatly reduced mobility of the compound and other molecules within the amorphous glassy composition. As long as the amorphous solid structure is maintained at a temperature below its glass transition temperature and the residual moisture remains relatively low, the probiotic bacteria can remain relatively stable. See FIG. 15. It should be noted that achieving a glassy structure is not a prerequisite for long term stability as some biological materials may fare better in a more crystalline state.

The dried glassy structure can be used en bloc, cut into desired shapes and sizes, or crushed and milled into a free flowing powder that provides easy downstream processing like wet or dry agglomeration, granulation, tableting, compaction, pelletization or any other kind of delivery process. Processes for crushing, milling, grinding or pulverizing are well known in the art. For example, a hammer mill, an air mill, an impact mill, a jet mill, a pin mill, a Wiley mill, or similar milling device can be used. A suitable exemplary particle size is less than about 1000 µm and in some embodiments less than 500 µm.

In another example of the present invention, the dry stable powder containing bioactive material is agglomerated with molten fats. The dry powder is placed in a planetary mixer at 40° C. and molten fats such as cocoa butter, natural waxes or hydrogenated oil or a mixture thereof are slowly added to the warm powder under mixing and the mixture is cooled down to below the melting temperature of the fats while mixing continue until a visually uniform size of agglomerated powder is achieved. The weight mass of the molten fats mixture in the composition is between about 20% and about 70%, in some embodiments about 30-50%. The final product can be consumed in an agglomerated form or compressed in a tablet press machine and consumed in a tablet form.

In one particular example the dry powder is compressed in a tablet press machine to form a tablet in a desirable shape and size. The stable and dry biological composition is optionally mixed with a filler to adjust the potency of the tablet to a desirable dosage. The filler may include, but is not limited to, maltodextrin, sodium carboxymethylcellulose, calcium carboxy-methylcellulose, colloidal silica dioxide, and combinations thereof. Optionally, a disintegration-promoting agent is also included in the tableting mix. Examples of a disintegration-promoting agent may include, but are not limited to, sodium croscarmellose, crospovidone (insoluble polyvinylpyrrolidone), sodium starch gycolate, sodium starch glyconate, pregelatinized starch and the like. As used herein, the tableting mixture may optionally include flow agents. The flow agents may include, but are not limited to, magnesium stearate, calcium stearate, zinc state, stearic acid and fumed silica such as hydrophilic or hydrophobic fumed silica.

Suitable methods for producing tablets from the stable biological composition and other tablet ingredients include standard press tableting methods, including those conventionally used for producing multi-layer tablets. Tableting compressing pressure of up to 50 kN/cm2, corresponding to a tensile strength below 100N (Erweka equipment) is preferable, however temperature exposure should be limited to below 60° C. in those cases where the biological material is a live microorganism.

The tablets may be designed to be swallowed whole, chewed or consumed as effervescent drink tablets. When the tablets disintegrate on consumption, whether in the mouth, in the drink or in the stomach, the biological material is exposed to other active materials from which they were held separate by the tablet structure. This may potentially harm the biological material if the local concentration of the damaging materials is too high. It is therefore preferred in some embodiments that the disintegration of the biological active material is delayed to allow the contents of other active components in the tablet to be diluted and dispersed. This problem was resolved in the present invention by forming hardened or cross-linked structured composition as described herein. In some embodiments, the biological material remains intact within the composition matrix upon mixing in water. In some embodiments, the biological material is released unharmed from the composition matrix at a desired site of action along the digestive tract of the animal.

Tablets according to the invention may be packaged in such a way as to preserve their initial state of dryness within acceptable limits. This may involve packaging the tablets in a moisture impermeable compartment such as a tube or a blister pack or a container containing a desiccant agent such as silica gel for absorbing water so as to reduce the water activity within the container. For protection against oxygen such a pack may also contain an oxygen scavenger material such as FreshPax®, Ageless™, ascorbyl palmitate or other ascorbates, propyl galates or other gallates, alpha-tocopherol, magnesium or sodium sulfite, butylated hydroxyanisole or butylated hydroxytoluene and the like.

The compositions and methods described herein stabilize the biological material and preserve its activity for an extended storage period at above ambient temperature and relative humidity. For example, the compositions are tested for stability by subjecting them at elevated temperature (e.g., 40° C.) and high humidity (e.g., 33% RH, or 43% RH) and measuring the biological activity of the formulations. As an example for live probiotic bacteria, results of these studies demonstrate that the bacteria formulated in these compositions are stable for at least 60 days. Stability is defined as time for one log CFU/g potency loss. Such formulations are stable even when high concentrations of the biologically active material are used. Thus, these formulations are advantageous in that they may be shipped and stored at temperatures at or above room temperature for long periods of time.

EXAMPLES

Example 1

Preparation of Dry and Stable Composition

Basic Carbohydrates Mixture
About 70 g of trehalose (Cargill Minneapolis, Minn.), about 5 g of instant Inulin (Cargill Minneapolis, Minn.) and about 3 g of sodium alginate (ISP Corp., Wayne, N.J.) were uniformly mixed in dry form.
Basic Glass Enhancers Mixture
About 17 g of casein hydrolysate or pea hydrolysate (ultra filtrated hydrolysates, Marcor, Carlstadt, N.J.) and 5 g of sodium citrate or sodium ascorbate (Sigma, St. Louis, Mo.) were uniformly mixed in dry form.
Stabilization of Probiotic Bacteria
Fresh concentrate of *Lactobacillus rhamnosus*. (100 ml at 10% solids, direct from fermentation harvest) was added in a blender and maintained at 35° C. About 78 g of basic carbohydrates mixture and about 22 g of the basic glass enhancer mixture were slowly added to the probiotic culture and mixing was carried out at 35° C. for 10 minutes. The viscous slurry was then transferred to a vessel having a perforated bottom and allowed dripping into a bath containing liquid nitrogen. The beads were then removed from the liquid nitrogen and immediately transferred to drying.
Drying of the Frozen Beads Containing Probiotic Bacteria
The frozen beads were spread on a tray at a loading capacity of 200 g/sq ft and immediately placed on a shelf in a freeze drier (Model 25 SRC, Virtis, Gardiner, N.Y.). Vacuum was then adjusted to between 2000-2700 mTORR and shelf temperature raised to +30° C. These temperature and vacuum pressure settings were maintained for 5 hours. Optionally, the temperature of the frozen beads was acclimatized to about −20° C. before initiating the primary liquid drying by applying a vacuum pressure at about 1000 mTORR and allowing the solid frozen beads to purge for about 10 minutes. The primary drying step was then followed by adjusting the vacuum pressure to between 2000-2700 mTORR and shelf temperature raised to +30° C. These temperature and vacuum pressure settings were maintained for 5 hours. A secondary drying step was then followed at full vacuum (150-200 mTORR) and shelf temperature maintained at between 30° C. and 50° C. for additional 3 hours. The formulation was completely dried and its water activity measured by a Hygropalm Aw1 instrument (Rotonic Instrument Corp., Huntington, N.Y.) at Aw=0.23.

Example 2

Storage Stability of the Dry Probiotic Bacteria

FIG. 1 shows the storage stability under two different accelerated storage conditions of 40° C. and 33% RH and 30° C. and 43% RH of dry stable probiotic bacteria from Example 1 and commercially available dry probiotic bacteria (Culturelle, Amerifit, Inc., Cromwell, Conn.). The commercial probiotic bacteria completely lost its viability within the first few weeks under the accelerated storage conditions, while the dry composition of the probiotic bacteria of the present invention lost only 1.18 logs after 60 days at 30° C. and 43% RH and only 1.09 logs at 40° C. and 33% RH.

Example 3

Scale-Up Production of Stable Dry Composition Containing Probiotic Bacteria *Lactobacillus rhamnosus*

*Lactobacillus rhamnosus* (400 g frozen concentrate from a commercial source) was thawed at 37° C. in a jacketed dual planetary mixer (DPM, 1 qt, Ross Engineering, Inc. Savannah, Ga.,) and the solid content adjusted to 10% solids wt with distilled water). About 212 g of trehalose (Cargill Minneapolis, Minn.), about 20 g of instant Inulin (Cargill Minneapolis, Minn.), about 12 g of sodium alginate (ISP Corp., Wayne, N.J.), about 136 g of casein hydrolysate (ultra filtrated hydrolysates, Marcor, Carlstadt, N.J.) and about 20 g of sodium ascorbate (Sigma, St. Louis, Mo.) were uniformly mixed in dry form. The powders mixture was slowly added to the probiotic culture and mixing was carried out at 40 RPM and 37° C. for 10 minutes. The slurry was then transferred to a vessel having a perforated bottom and allowed to drip into a bath containing liquid nitrogen. The beads were then removed from the liquid nitrogen, placed in sealed aluminum foiled bag and stored in a deep freezer at −80° C. for several weeks.

For drying, the frozen beads were evenly spread on trays at a loading capacity ranging from 500 up to 1500 g/sq ft and the trays placed on shelves in a freeze drier (Model 25 SRC, Virtis, Gardiner, N.Y.). A primary liquid drying step was started by adjusting the vacuum pressure to between 2000-2700 mTORR and product temperature raised and stabilized between −10 and −5° C. Over time (about 10-16 h) the product temperature increased to about 20 to 25° C. at which point a secondary drying step initiated at maximum vacuum (150-200 mTORR) and product temperature maintained at between 30 to 40° C. for additional 14 hours. The formulation was completely dried and its water activity measured at 0.23 Aw.

Example 4

Scale-Up Production of Stable Dry Composition Containing Probiotic Bacteria *Bifidobacterium lactis*

*Bifidobacterium lactis* (400 g frozen concentrate from a commercial source) was thawed at 37° C. in a jacketed dual planetary mixer (DPM, 1 qt, Ross Engineering, Inc. Savannah, Ga.). About 212 g of trehalose (Cargill Minneapolis, Minn.), about 20 g of instant Inulin (Cargill Minneapolis, Minn.), about 12 g of sodium alginate (ISP Corp., Wayne, N.J.) and about 20 g of sodium ascorbate (Sigma, St. Louis, Mo.) were uniformly mixed in dry form. The powders mixture was slowly added to the probiotic culture. About 136 g of pea hydrolysate (ultra filtrated hydrolysates, Marcor, Carlstadt, N.J.) was dissolved in 80 g distilled water and the mixture shortly microwaved or warmed in a water bath to 60° C. until complete dissolution and then cooled down to about 35° C. The dry mix powder and the solution containing pea protein hydrolysate were added to the probiotic concentrate and mixing was carried out at 40 RPM and 37° C. for 20 minutes. The slurry was then transferred to a vessel having a perforated bottom and allowed to drip into a bath containing liquid nitrogen. The beads were then removed from the liquid nitrogen, placed in sealed aluminum foiled bag and stored in a deep freezer at −80° C. for several weeks.

For drying, the frozen beads were evenly spread on trays at a loading capacity of 800 g/sq ft and the trays placed on shelves in a freeze drier (Model 25 SRC, Virtis, Gardiner, N.Y.). A primary liquid drying step was started by adjusting the vacuum pressure to between 2000-2700 mTORR and product temperature raised and stabilized between −10 and −5° C. Over time (about 10-16 h) the product temperature increased to about 20 to 25° C. at which point a secondary drying step initiated at maximum vacuum (150-200 mTORR) and product temperature maintained at between 30 to 40° C. for additional 14 hours. The formulation was completely dried and its water activity measured at 0.23 Aw.

Example 5

Preparation of a Hydrogel Formulation Containing Probiotic Bacteria *Bifidobacterium lactis*

Concentrated probiotic slurry of *Bifidobacterium lactis* is prepared according to Example 1. To the basic formulation, 0.5 g of dibasic calcium phosphate is added, followed by 0.5 g of gluconolactone. The slurry is allowed to harden at room temperature over the next 2 hours to form a solid hydrogel. The firm gel is sliced to thin and long threads, using a commercially available slicer/shredder. The thin threads are directly loaded on trays in wet form or snap-frozen in liquid nitrogen and loaded on a tray at a loading capacity of 500 g/sq ft and placed in a freeze drier for drying as described in Example 3. The water activity (Aw) of the formulation is 0.05 (Measured by HygroPalm Aw1, Rotonic Huntington, N.Y.). The dry formulation is further ground to fine powder using standard hammer milling equipment and sieved through 50-250 micron screens.

Example 6

Figure 2:
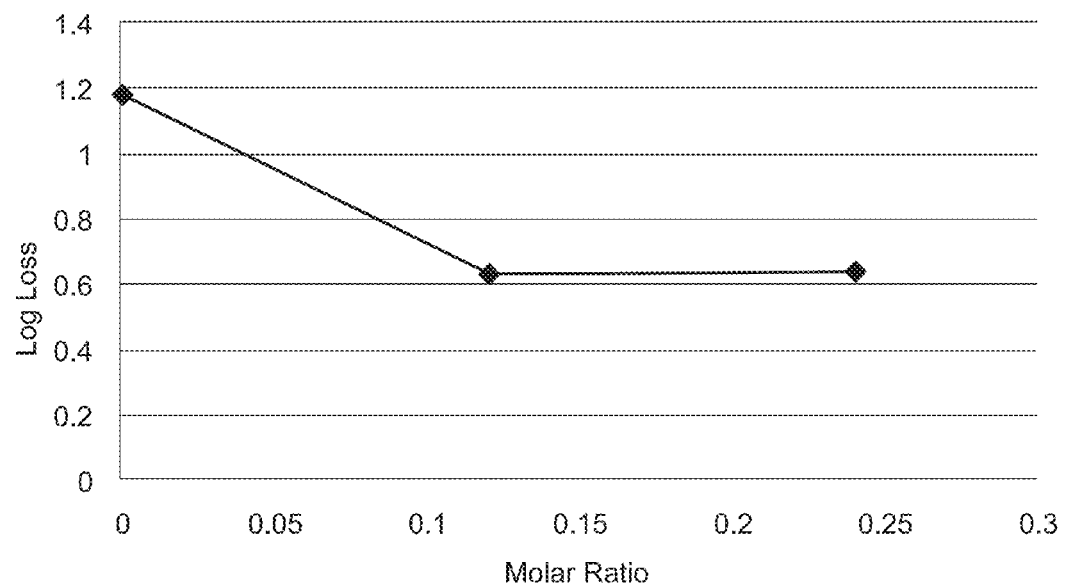
FIG. 2 shows the effect of various molar ratios between the glass enhancers and carbohydrates mixture in the composition on probiotic stability (*L. paracasei*) under accelerated storage conditions (37° C. and 33% RH).

Optimization of the Molar Ratio Between the Glass Enhancers and Carbohydrates Mixture Several compositions containing various molar proportions of glass enhancers and carbohydrates mixture were prepared according to Example 1. A concentrated culture of the probiotic bacteria *L. paracasei* was obtained from a commercial source and prepared in a dry composition as described in Example 1 except that the slurry was immediately loaded on trays in wet form without snap-freezing and purging steps. The slurry was dried in primary and secondary stages as described in Examples 1 and 3 except that the shelf temperature was raised to 40° C. during primary and secondary drying stages. The stable powder was subjected to acceleration storage conditions at 37° C. and 33% RH for 84 days. FIG. 2 show the effect of various molar ratios on the stability of the dried bacteria. Results suggested that optimal molar ratio between the glass enhancers and the carbohydrates mixture is about 0.12-0.15.

Example 7

Effect of the Composition of the Current Invention on Storage Stability of the Probiotic Bacteria *L. acidophilus*

Figure 3:
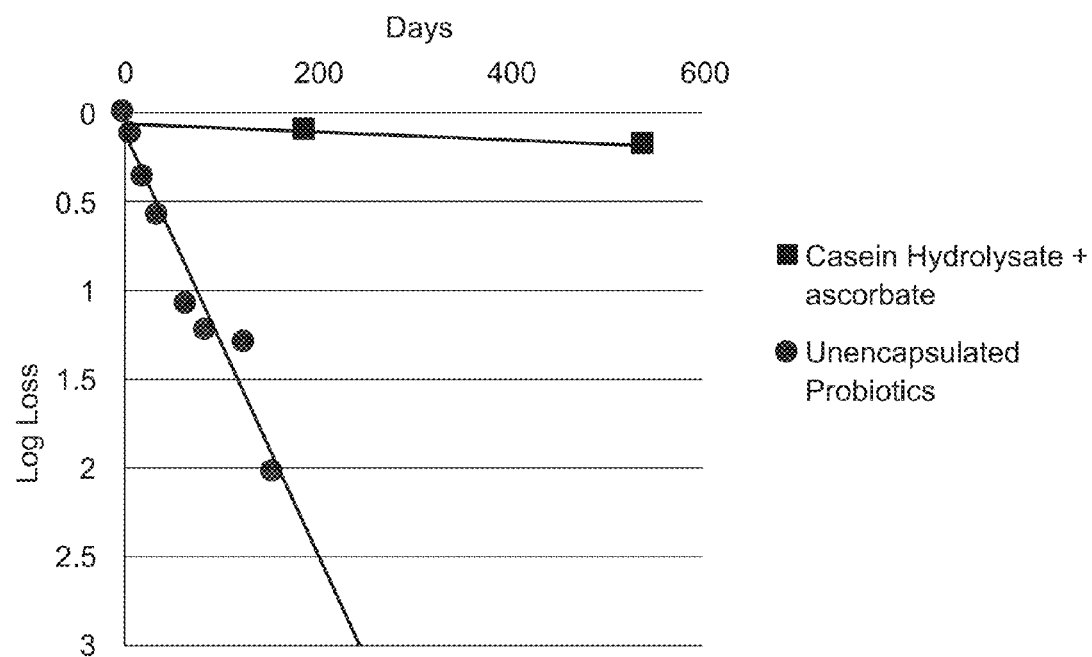
FIG. 3 shows the effect of the composition of the current invention on storage stability of the probiotic bacteria *L. acidophilus*. The stability of the dry probiotic bacteria was tested at accelerated storage conditions of 24° C. and 33% RH for 537 days.

A composition containing carbohydrates mixture and glass enhancers mixture as described in Example 1 was prepared. A concentrated culture of the probiotic bacteria *L. acidophilus* was obtained from a commercial source and prepared in a dry composition as described in Examples 1 and 3 and the stable powder was subjected to acceleration storage conditions at 24° C. and 33% RH for 537 days. FIG. 3 demonstrates the superior stability of the probiotic formulated with the composition of the current invention. Results show that the probiotic viability reduced by only 0.18 log over 537 days of shelf storage under the specified conditions.

Example 8

Effect of Various Glass Enhancers Compounds on Storage Stability of the Probiotic Bacteria *L. acidophilus*

Figure 4:
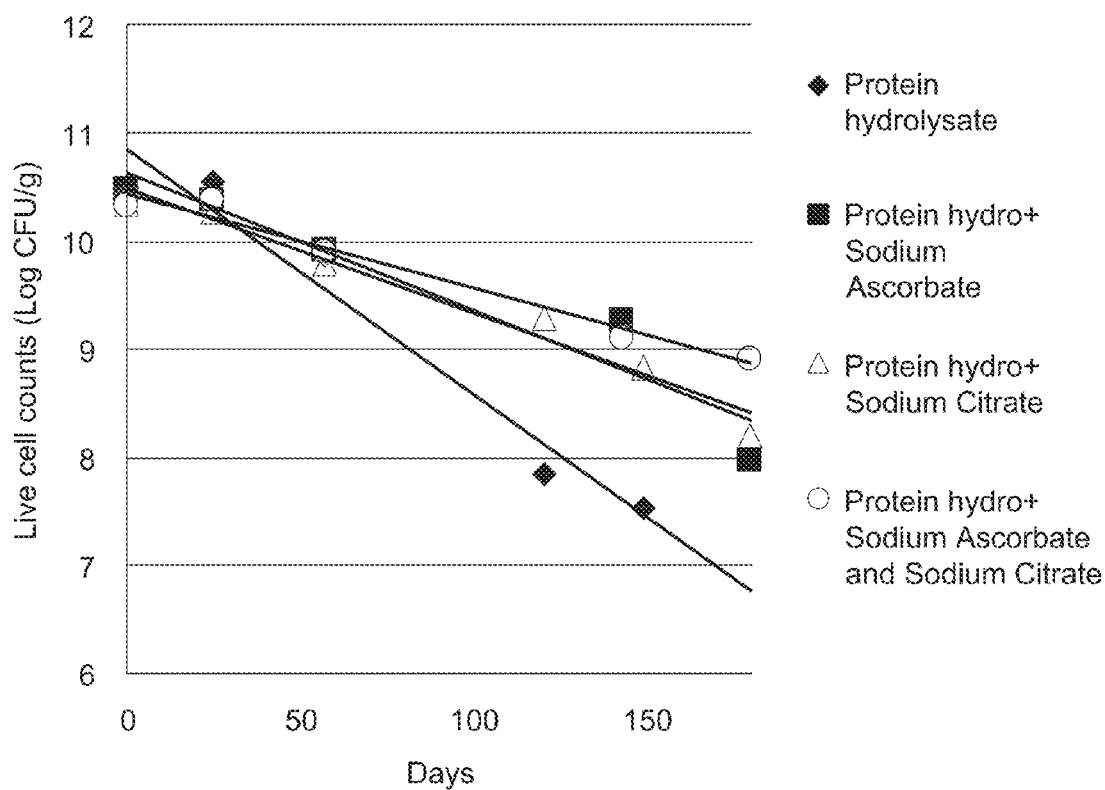
FIG. 4 shows the effect of various glass enhancers compounds on storage stability of the probiotic bacteria *L. acidophilus*. The stability of the dry probiotic bacteria was tested at accelerated storage conditions of 24° C. and 43% RH for 180 days.
Figure 5:
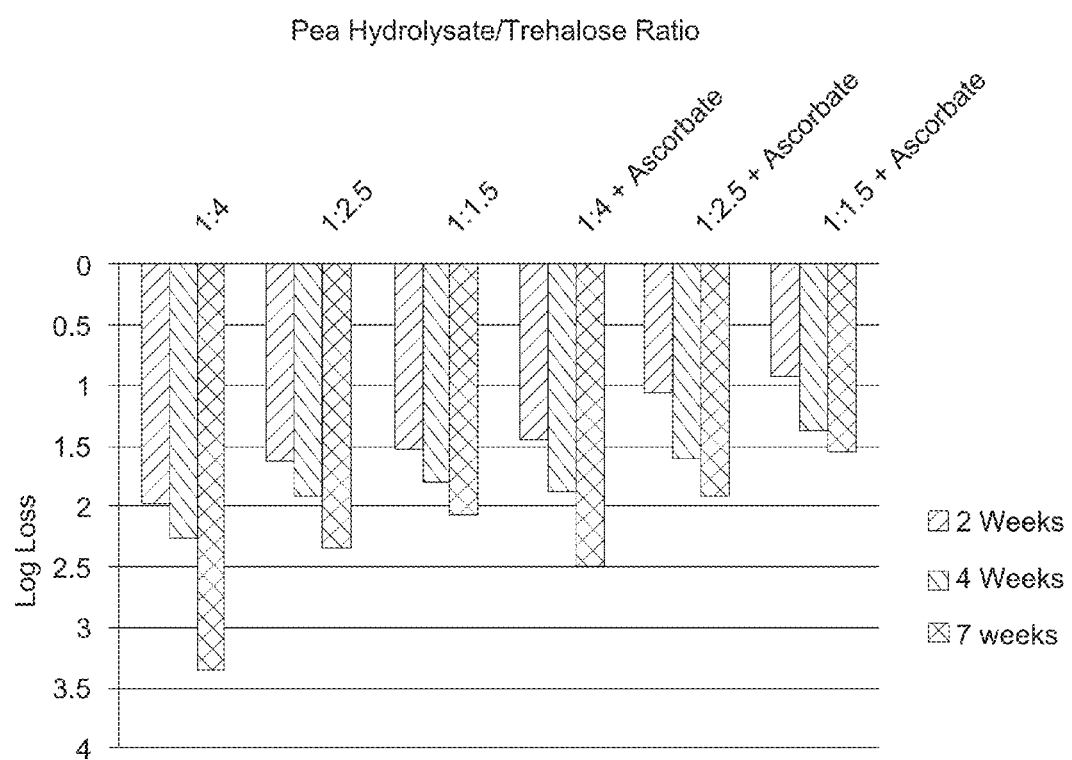
FIG. 5 shows the effect of various protein hydrolysate/sugar ratios on storage stability (35° C. and 43% RH) of the probiotic bacteria *Bifidobacterium lactis*.
Figure 6:
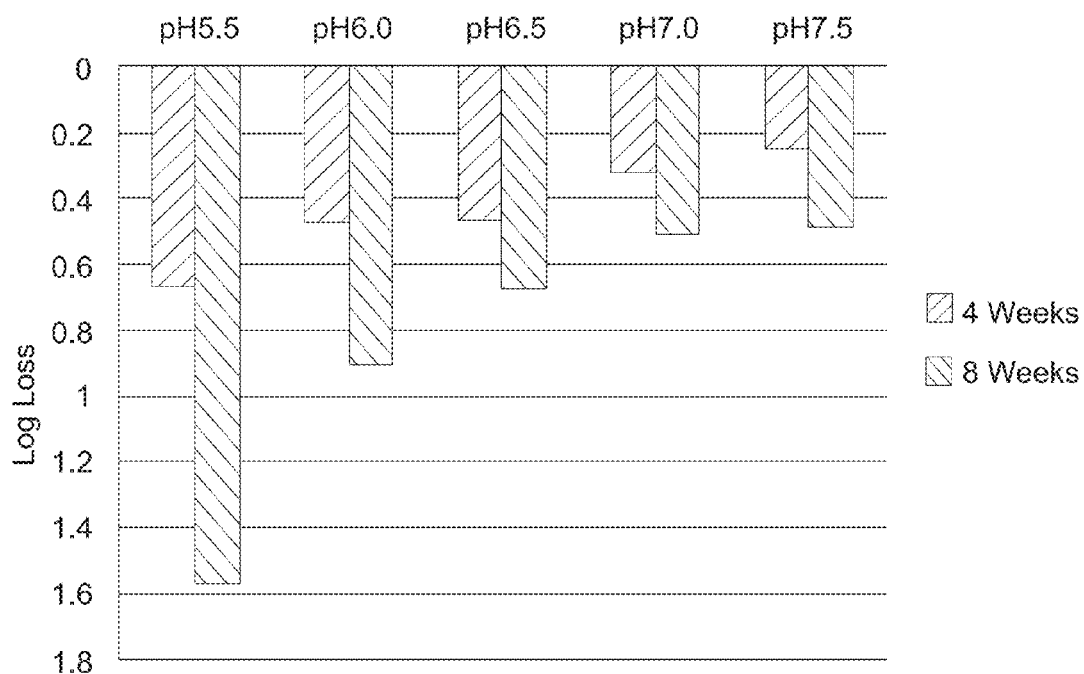
FIG. 6 shows pH optimization for maximum stability of the probiotic *L. rhamnosus* (acceleration storage conditions at 40° C. and 33% RH for 8 weeks).

Several composition containing carbohydrates mixture as described in Example 1 and glass enhancers mixture containing casein hydrolysate and sodium citrate or sodium ascorbate or a combination of both were prepared. A concentrated culture of the probiotic bacteria *L. acidophilus* was obtained from a commercial source and prepared in a dry composition as described in Example 1 except that the slurry was immediately loaded on trays in wet form without snap-freezing and purging steps. The slurry was dried in primary and secondary stages as described in Examples 1 and 3 and the stable powder was subjected to acceleration storage conditions at 24° C. and 43% RH for 180 days. FIG. 4 show the effect of various glass enhancing compounds on the stability of the dried bacteria. Results suggested that a significant better stability was obtained by the inclusion of additional glass enhancer on top of the protein hydrolysate. In particular, the inclusion of equal amounts of sodium acetate and sodium ascorbate provided the most stable composition. Results from both Examples 5 and 6 also suggested that various glass enhancers may be more effective or even may act as a destabilize depending on the bacterial strain.

Example 9

Effect of Various Protein Hydrolysate/Sugar Ratios on Storage Stability of the Probiotic Bacteria *Bifidobacterium lactis*

Several compositions containing carbohydrates mixture and glass enhancers as described in Example 1 and compositions containing equal amounts but at various ratios of pea hydrolysate/trehalose with or without sodium ascorbate were prepared. A concentrated culture of the probiotic bacteria *Bifidobacterium lactis* was obtained from a commercial source and prepared in a dry composition as described in Examples 1 and 3 and the stable powder was subjected to acceleration storage conditions at 35° C. and 43% RH for 7 weeks. FIG. 5 show the effect of 1:4, 1:2.5 and 1:1.5 ratios of pea hydrolysate/trehalose with or without sodium ascorbate on the stability of the dried bacteria. Results suggested that a significant better stability was obtained at increasing ratios of pea hydrolysate/trehalose. In particular, a ratio of 1:1.5 pea hydrolysate/trehalose provided more stable composition. Inclusion of sodium ascorbate at higher pea hydrolysate/trehalose ratio resulted in superior stability compared to sodium ascorbate excluded formulations.

Example 10 pH Optimization for Maximum Stability of the Probiotic *L. rhamnosus*

Several compositions containing carbohydrates mixture and glass enhancers as described in Example 1 at different pHs were prepared. A concentrated culture of the probiotic bacteria *L. rhamnosus* was obtained from a commercial source and prepared in a dry composition as described in Examples 1 and 3. The stable powder was subjected to acceleration storage conditions at 40° C. and 33% RH for 8 weeks. FIG. 6 show the pH effect of the slurry on the stability of the dried bacteria. Results suggested that optimal stability was achieved at neutral pH (~7).

Example 11

Stable Dry Powder Containing an Enzyme

A hydrogel formula containing 40 weight percent of phitase (BASF, GmBH) is prepared by mixing 400 g of the carbohydrates mixture and 200 g of the glass enhancers mixture as described in Examples 1 and 4 and 400 g of phitase in 1000 ml of water. The shredded hydrogel formulation is snap-frozen in liquid nitrogen and dried in a vacuum oven at a primary and secondary drying temperature of 50° C. For determination of loading and storage stability of the dried formula: a dry sample is accurately weighed (<100 mg) in a microcentrifuge tube. A 200 μl portion of dimethyl sulfoxide (DMSO) is added. The formulation is dissolved in the DMSO buffer by vortexing. To this sample, 0.8 ml of a solution containing 0.05 N NaOH, 0.5% SDS and 0.075 M Citric acid (trisodium salt) is added. The tubes are sonicated for 10 min at 45° C., followed by a brief centrifugation at 5,000 rpm for 10 min. Aliquots of the clear DMSO/NaOH/SDS/Citrate solution are taken into wells of a microplate and analyzed for protein content using the Bradford assay method. The stability of the stable enzyme dry composition after exposure to 95° C. for 20 min is significantly higher than a dry enzyme without the composition of the present invention.

Example 12

Stable Dry Powder Containing an Infectious Salmon Anemia Virus (ISAV) Vaccine

Concentrated slurry of ISAV vaccine (Novozyme, Denmark) is prepared according to Example 4 except that 20 ml 4% chitosan solution in 0.5% acetic acid was added to the slurry containing the ISAV vaccine concentrate, the carbohydrates mixture and the glass enhancers. 0.5 g of dibasic calcium phosphate is added, followed by 0.5 g of glucono-lactone. The slurry is allowed to harden at room temperature over the next 2 hours to form a solid hydrogel. The firm gel is sliced to thin and long threads, using a commercially available slicer/shredder. The thin threads are directly loaded on trays in wet form or snap-frozen in liquid nitrogen and loaded on a tray at a loading capacity of 1500 g/sq ft and placed in a freeze drier for drying as described in Example 3. The water activity (Aw) of the formulation is 0.25. The dry formulation is further ground to fine powder using standard hammer milling equipment and sieved through 50-150 micron screens. The stable dry ISAV composition is used for oral vaccination by top coating a commercial feed with the dry composition and feeding to Atlantic salmon fish.

Example 13

Preparation of Invasive Species Bait

Pelleted bait for specifically targeted invasive species according to the present invention is prepared containing a pesticide. 200 g of a formulation as described in Example 9 is prepared and added to 200 gm of water. To this solution is added 90 gm of Rotenone and 0.5 gm of calcium phosphate dibasic, followed by 0.5 gm of gluconolactone. The slurry is immediately spray dried in a standard industrial pray drier, and the dry formulation is used for targeting specific invasive species without deleterious effect of the toxin on the environment or close-by ecosystems.

Example 14

Preparation of a Protected Plant Probiotic Formulation

A biological control agent such as *Rhizobacteria* is prepared in dry composition according to Example 4. The effectiveness of the dry *Rhizobacteria* composition is evaluated on lettuce growth under gnotobiotic conditions. Doses of 100 mg of *Rhizobacteria* dry composition per plant are inoculated into jars with sand and planted with pre-geminated (24 h) lettuce seedlings. A nutrient dose of 5 ml of sterilized Hoagland solution is applied to the plants in the jar. Jars are arranged randomly in growth chamber maintained at 28° C. with 12 h photoperiod. During every 7 days interval after inoculation, plants and adhering sand are carefully removed from the jars. Roots are washed in sterile phosphate buffer (pH 7.0), and measurement of root length is recorded.

Example 15

Preparation of Dry and Stable Probiotic Substance

Basic Formulation
A 75 g portion of trehalose (Cargill Minneapolis, Minn.) and 22 g of extensively hydrolyzed casein (Marcor, Carlstadt, N.J.) were uniformly mixed with 3 g of sodium alginate (ISP Corp., Wayne, N.J.) in dry form. Fresh concentrate of *Lactobacillus acidophilus* (100 ml containing at least 10% solids, direct from fermentation harvest) was added in a blender and maintained at 35° C. The dry mix of the gum, sugar and hydrolyzed protein was slowly added to the probiotic culture and mixing was carried out at 35° C. for 10 minutes. The viscous slurry was then transferred to a vessel having a perforated bottom and allowed to drip into a bath containing nitrogen. The beads were then removed from the liquid nitrogen and immediately transferred to drying.

Drying of the Frozen Beads of the Basic Formulation
The frozen beads were evenly spread on a tray at a loading capacity of 100 g/sq ft and immediately placed on a shelf in a freeze drier (Model 25 SRC, Virtis, Gardiner, N.Y.). Vacuum pressure was then applied at 1000 mTORR and the solid frozen beads were allowed to purge for 10 minutes. Vacuum was then adjusted to 2700 mTORR and shelf temperature raised to +30° C. These temperature and vacuum pressure were maintained for 3 hours. A secondary drying step was then followed at full vacuum (150-200 mTORR) and shelf temperature raised to 30° C. for additional 2 hours. The formulation was completely dried and its water activity measured by a Hygropalm Aw1 instrument (Rotonic Instrument Corp., Huntington, N.Y.) at Aw=0.23.

Example 16

Stable Dry Composition Containing Probiotic Bacteria *Lactobacillus rhamnosus* LGG

*Lactobacillus rhamnosus* LGG (500 g frozen concentrate from a commercial source) was thawed at 37° C. in a jacketed dual planetary mixer (DPM, 1 qt, Ross Engineering, Inc. Savannah, Ga.,). Two glass forming agents; trehalose (387 g, Cargill Minneapolis, Minn.) and extensively hydrolyzed casein (83 g, Marcor, Carlstadt, N.J.) were homogenously mixed in dry form with two matrix forming agents; sodium alginate (15 g, ISP Corp., Wayne, N.J.) and instant Inulin (25 g, Cargill Minneapolis, Minn.). The dry mix was slowly added to the thawed probiotic bacteria and mixing was carried out at 40 RPM and 37° C. for 10 minutes. The viscosity of the slurry was adjusted to 12,000 Cp by the addition of 50-200 ml of water. The slurry was then transferred to a vessel having a perforated bottom and allowed to drip into a vessel containing liquid nitrogen. The beads were then removed from the liquid nitrogen, placed in sealed aluminum foiled bag and stored in a deep freezer at −80° C. for several weeks.

Figure 13:
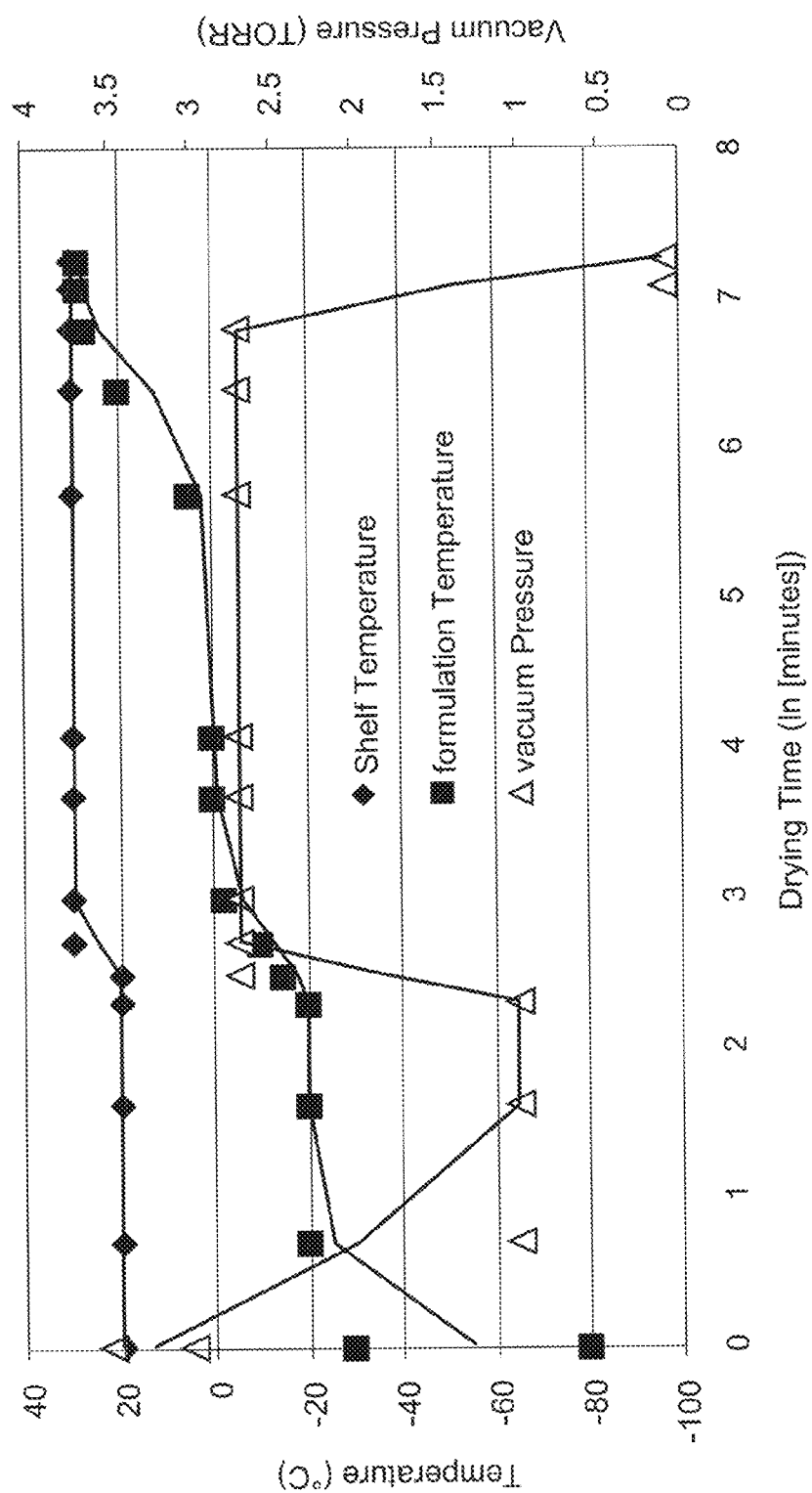
FIG. 13. Drying profile in a freeze drier of the composition according to the method of the invention.

For drying, the frozen beads were evenly spread on trays at a loading capacity ranging from 100 up to 500 g/sq ft and the trays placed on shelves in a freeze drier (Model 25 SRC, Virtis, Gardiner, N.Y.). Vacuum pressure was applied at 1000 mTorr and shelf temperature adjusted to +20° C. The solid frozen beads were allowed to purge for a time period ranging from 1 to 30 minutes. The purging step was followed by a primary drying step after adjusting the vacuum pressure to 2700 mTORR and shelf temperature raised to +30° C. These temperature and vacuum pressure were maintained for 12 hours. A secondary drying step was then followed at full vacuum (150-200 mTORR) and shelf temperature maintained at 30° C. for additional 4 hours. The formulation was completely dried and its water activity measured at 0.23 Aw. FIG. 13 shows the drying profile of the probiotic formulation.

Figure 10:
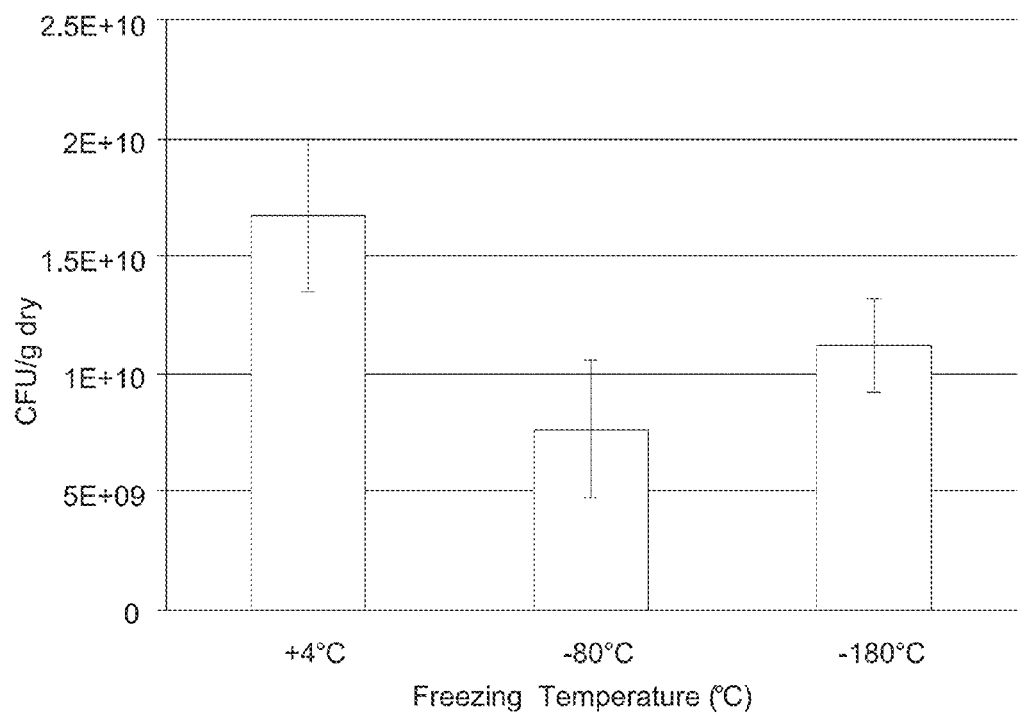
FIG. 10. The effect of freezing temperature of a composition containing *L. rhamnosus* as frozen solid beads in liquid nitrogen or −80° C. deep freezer and as non-frozen viscous slurry at +4° C. on the bacterial initial CFU counts in the dry composition. Results show only the effect of freezing temperature of the slurry with no additional step of purging before drying.
Figure 11:
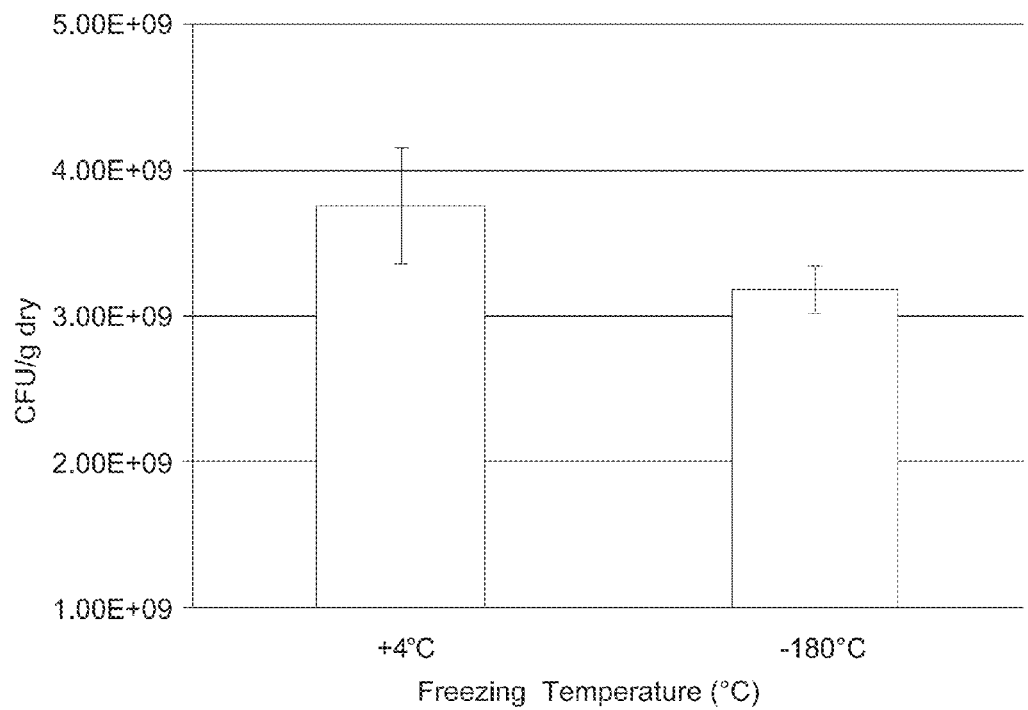
FIG. 11. The effect of freezing temperature of a composition containing *Bifidobacterium animalis* as frozen solid beads in liquid nitrogen and as non-frozen viscous slurry at +4° C. on the bacterial initial CFU counts in the dry composition. Results show only the effect of freezing temperature of the slurry with no additional step of purging before drying.

The viability losses after freezing the slurry at different temperatures (+4° C., −80° C. and −180° C.) and after the drying process including preparation of frozen beads, and drying in a freeze-drier are presented in FIGS. 10, 11 and 14. Viability losses for the entire process were generally lower than <1 log depending on the type of bacterial culture (frozen or dry cultures) and on the freezing temperature of the viscous slurry. Results show that snap-freezing of the probiotic bacteria in liquid nitrogen (−180° C.) was a less damaging process than freezing at −80° C.

Figure 12:
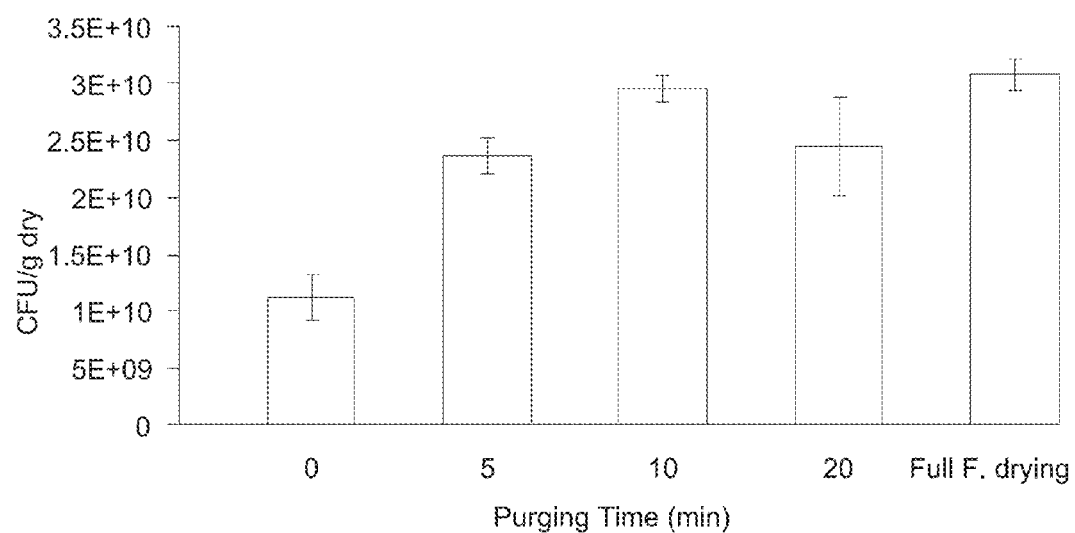
FIG. 12. The effect of purging duration under vacuum of frozen solid beads on initial CFU counts of *L. rhamnosus* in a dry composition.

FIGS. 12 & 15 show the effect of various purging time periods ranging from 0 min (no purging) to 30 min on initial counts of probiotic bacteria in the dry composition and on

Example 17

Trehalose (752 g, Cargill Minneapolis, Minn.), extensively hydrolyzed Pea protein (167 g, Marcor, Carlstadt, N.J.), sodium alginate (30 g, ISP Corp., Wayne, N.J.) and instant Inulin 50 g, Cargill Minneapolis, Minn.) were homogenously blended in dry form. The dry mix was slowly added to 1000 ml hot de-ionized water at 80° C. in a jacketed dual planetary mixer (DPM, 1 qt, Ross Engineering, Inc. Savannah, Ga.,) and mixing was carried out at 40 RPM for 10 minutes. The mixture temperature was reduced to 37° C. and 100 g dry powder of *Lactobacillus rhamnosus* LGG obtained from a commercial source was slowly added and mixing continued for 20 minutes. The slurry was then extruded through a 2 mm orifice needle into a bath containing liquid nitrogen. The /strings/beads were then removed from the liquid nitrogen placed in sealed aluminum foiled bag and stored in a deep freezer at −80° C. for several weeks. For drying, the frozen strings/beads were evenly spread on trays at a loading capacity ranging from 100 to 500 g/sq ft and the trays placed on shelves in a freeze drier (Model 25 SRC, Virtis, Gardiner, N.Y.) and dried as described in Example 16. All formulations were contentedly retained within the tray and no splattering or foaming was observed in all loading levels. The formulation was completely dried even at the higher loading capacity and water activity measured at 0.26 Aw and lower for all samples.

Example 18

Preparation of a Hydrogel Formulation Containing Probiotic Bacteria *Bifidobacterium* sp.

Concentrated probiotic slurry of *Bifidobacterium* sp. is prepared according to Example 15. To the basic formulation, 0.5 g of dibasic calcium phosphate is added, followed by 0.5 g of gluconolactone. The slurry was allowed to harden at room temperature over the next 2 hours to form a solid hydrogel. The firm gel was sliced to thin and long threads, using a commercially available slicer/shredder. The thin threads are snap-frozen in liquid nitrogen and loaded on a tray at a loading capacity of 700 g/sq ft and placed in a freeze drier for drying as described in Example 16. The water activity (Aw) of the formulation was 0.05 (Measured by HygroPalm Aw1, Rotonic Huntington, N.Y.). The dry formulation was further ground to fine powder using standard hammer milling equipment and sieved through 50-250 micron screens.

Example 19

Allergen Free Composition Containing Probiotic Bacteria *Lactobacillus acidophilus*

Trehalose (752 g, Cargill Minneapolis, Minn.), extensively hydrolyzed Pea protein (167 g, Marcor, Carlstadt, N.J.), sodium alginate (30 g, ISP Corp., Wayne, N.J.) and instant Inulin 50 g, Cargill Minneapolis, Minn.) were homogenously blended in dry form. The dry mix was sterilized by slowly adding to 1000 ml hot de-ionized water at 80° C. in a jacketed dual planetary mixer (DPM, 1 qt, Ross Engineering, Inc. Savannah, Ga.,) and mixing was carried out at 40 RPM for 10 minutes until smooth and clear slurry is formed. The mixture temperature was reduced to 37° C. and 1000 g frozen beads containing *Lactobacillus acidophilus* obtained from a commercial source was slowly added and mixing continued for 10 minutes. The slurry was then extruded through a 2 mm orifice needle into a bath containing liquid nitrogen. The /strings/beads were then removed from the liquid nitrogen placed in sealed aluminum foiled bag and stored in a deep freezer at −80° C. for several weeks. For drying, the frozen strings/beads were evenly spread on trays at a loading capacity of 1000 g/sq ft and the trays placed on shelves in a freeze drier (Model 25 SRC, Virtis, Gardiner, N.Y.) and dried as described in Example 16. The initial CFU counts of the probiotic bacteria in the dry composition was 10.53 logs/g, and viability loss after 42 days storage under accelerated storage conditions of 40° C. and 33% RH was 0.69 log CFU/g.

Example 20

Infant Formula Containing the Dry Formulation of the Present Invention

A stable dry formulation containing *Lactobacillus rhamnosus* was prepared according to Example 16 followed by sieving into two particle size groups (above 50 μm and below 150 μm). An infant formula was prepared by mixing 99.9 g of Nutramigen (Mead Johnson; Evansville, Ill.) with 0.1 g of the dry formulation particles in the size range between 50 μm and 150 μm). The final product contains about $10^8$ cfu of *Lactobacillus rhamnosus* per 100 g infant formula.

Example 21

Probiotic Supplement Containing the Stable Dry Formulation of the Invention A stable dry composition containing *Lactobacillus acidophilus* is formulated into oral dosage forms, such as tablets, caplets, or capsules. Orange flavored tablets containing 99.9 g of a compression agent (dextrose) and 0.1 g of the dry formulation particles in the size range between 50 μm and 150 μm are prepared by direct compression on a rotary machine using a ½" round standard concave tooling. The final product contains about $10^8$ cfu/unit dose. Hardness of the tablets is in the range of 8-10 kp and disintegration times is approximately 20 seconds. The compressed tablets are packaged into 180 cc HDPE bottles of 100 tablets each and exposed to controlled temperature/humidity of 40° C./33% RH. The product is subjected to monthly microbiological stability testing over a period of 12 months or until a reduction in the assay count below $1\times10^6$/unit dose is observed.

Example 22

A Functional Beverage Drink Containing the Stable Dry Formulation of the Present Invention A dry mix containing (% by weight) 71% sucrose, 14% maltodextrin, 10% inulin, 2% dextrose, 1% citric acid anhydrous, 0.3% gum acacia, 0.3% flavors, 0.3% Tricalcium phosphate and 0.1% dry probiotic formulation particles (*L. acidophilus*) in the size range between 50 μm and 250 μm is prepared. The final product contains about $10^9$ cfu/unit dose (30 g dry mix). The product is packaged in small aluminum foil bags (30 g unit dose/bag) for drinking by stirring in 340 mil water. The stability of the probiotic bacteria in the beverage dry mix is subjected to monthly microbiological stability testing over a period of 12 months or until a reduction in the assay count below $1 \times 10^7$/unit dose is observed.

Example 23

Preparation of Probiotic Pet Food

A commercially available pelleted pet food for dogs is dried in a convection oven to a water activity of 0.1, and then coated with the stable probiotic dry formulation prepared as described in Example 17. The dry pellets are sprayed with about 5% of fat-based moisture barrier (a mixture of 40% chicken fat, 40% cocoa butter and 20% beeswax), mixed in a drum tumbler with the dry powder formulation (usually 0.1-0.5% of total pet food that provides a dosage of $10.\text{sup}.8$ CFU/g), and finally sprayed with additional coat of the fat-based moisture barrier. The total amount of coating is about 15% (of the pet food). Coating time is about 30 min.

Example 24

Preparation of Fish Feed with Several Probiotic Microorganisms

Pelleted feed for fish according to the present invention is prepared with a mixture of several probiotics. A stable dry probiotic formulation containing a mixture of *L. rhamnosus*, *L. acidophilus* and *Bifidobacterium lactis* is prepared as described in Example 15. A commercially available starter feed for salmon (Zeigler Bros., Gardners, Pa.) is first dried in a convection oven to a water activity of 0.1, and then coated with the probiotics formulation in a drum tumbler. The pellets (1000 g) are first sprayed with about 5% by weight of fat-based moisture barrier (a mixture of 40% fish oil, 40% cocoa butter and 20% beeswax), then mixed with 1 g of the stable dry probiotic formulation (to attain a dosage of $10^7$ cfu/g feed), and finally sprayed with additional coat of the fat-based moisture barrier. The total amount of coating is about 10% (of the fish feed).

Example 25

Stable Dry Powder Containing an Enzyme

A hydrogel formula containing 40 weight percent of Savinase (Novozymes, Denmark) is prepared by mixing 600 g of the formulation described in Example 18 and 400 g of savinase in 1000 g of water solution. The shredded hydrogel formulation is snap-frozen in liquid nitrogen and dried in a vacuum oven at a formulation drying temperature of 50° C. For determination of loading and storage stability of the dried formula: a dry sample is accurately weighed (<100 mg) in a microcentrifuge tube. 200 μm of dimethyl sulfoxide (DMSO) is added. The formulation is dissolved in the DMSO buffer by vortexing. To this sample, 0.8 ml of a solution containing 0.05 N NaOH, 0.5% SDS and 0.075 M Citric acid (trisodium salt) is added. The tubes are sonicated for 10 min at 45° C., followed by a brief centrifugation at 5,000 rpm for 10 min. Aliquots of the clear DMSO/NaOH/SDS/Citrate solution are taken into wells of a microplate and analyzed for protein content using the Bradford assay method. The storage stability of the stable enzyme formulation is significantly higher than a dry enzyme without the formulation of the present invention.

Example 26

Stable Dry Powder Containing Vitamin A

A formulation containing 30 weight percent of Vitamin A is prepared by mixing 320 g instant inulin, 320 g maltodextrin DE-1 (Tate&Lyle, London, UK), 50 g sodium carboxymethylcellulose (Ashland Aqualon Functional Ingredients, Wilmington, Del.), 10 g sodium ascorbate and 300 g of vitamin A crystalline (BASF Corp., Florham Park, N.J.) in 1000 g water. The wet formulation is spray-dried in a Mobile-Minor spray drier (GEA Process Engineering Inc., Columbia Md.) at inlet and outlet temperature of 180° C. and 80° C., respectively or snap-frozen in liquid nitrogen, then spread on trays at a loading capacity of 1000 g/sq ft and dried as described in Example 16. The vitamin-A composition is stable (>80%) at 40° C. and 75% RH for 3 months.

Example 27

Preparation of Carotenes in a Protected Formulation Having Enhanced Bioavailability A formulation that protects and enhances the bioavailability of carotenes that would otherwise be subject to oxidation by other ingredients in a feed during storage or after feeding an organism is prepared according to the formulation and the method of the present invention. A formulation containing 6 g of water soluble chitosan (LSK BioPartners, Inc. Salt Lake City, Utah) is dissolved in 200 g water. To this solution is added 90 g of natural astaxanthin (Naturose™, Cyanotech Corp., Kailua-Kona, Hi.) and the slurry is atomized or extruded into a bath containing 5% sodium tripolyphosphate. The hydrogeled microparticles or strings are allowed to harden at room temperature over 4 hours. The particles are removed from the cross-linking bath, washed with water and mixed with a dry blend of 90 g sucrose and 10 g extensively hydrolyzed casein. The sugar/protein loaded particles are snap-frozen and immediately placed on trays at 500 g/sq ft and lyophilized in a freeze dryer until water activity reduced to less than 0.3. The dry formulation is further milled to the desired size distribution and packaged.

Example 28

Preparation of Invasive Species Bait

Pelleted bait for specifically targeted invasive species is prepared according to the present invention. 200 g of a formulation containing a pesticide as described in Example 1 is prepared and added to 200 gm of water. To this solution is added 90 gm of Rotenone and 0.5 gm of calcium phosphate dibasic, followed by 0.5 gm of gluconolactone. The slurry is allowed to harden at room temperature over 2 hours. The firm gel is sliced to thin and long threads through a slicer/shredder. The thin threads are loaded on a tray and placed in a freeze dryer. Shelf temperature is set at −30° C. and the formulation allowed freezing before full vacuum is applied and shelf temperature rose to +60° C. for over-night drying. The dry formulation is ground to the appropriate size distribution for the bait size specification for the specific species targeted.

Example 29

Preparation of a Protected Pesticide in a Water Insoluble Formulation

A protected granular formulation of a pesticide that would otherwise be subject to decomposition by other ingredients in a formulation during storage or after application in the environment is prepared with the formulation and the method of the present invention. A formulation containing 6 g of pectin and 102 g sucrose is added to 200 g water. To this solution is added 90 g of a dry formulation of a sensitive pesticide and a mixture containing 1.5 g of calcium phosphate dibasic and 0.5 g of calcium chloride, followed by 0.85 g of gluconolactone. The slurry is allowed to harden at room temperature over 4 hours, and then sliced to thin, long threads through a slicer/shredder. The thin threads are loaded on trays and dried in a freeze dryer to reach a water activity of 0.1. The dry formulation is further milled to the desired size distribution and packaged.

Example 30

Preparation of a Protected Plant Probiotic Formulation

A biological control agent such as *Rhizobacteria* is prepared in dry composition according to Example 18. The effectiveness of the dry *Rhizobacteria* composition is evaluated on lettuce growth under gnotobiotic conditions. Doses of 100 mg of *Rhizobacteria* dry composition per plant are inoculated into jars with sand and planted with pre-germinated (24 h) lettuce seedlings. A nutrient dose of 5 ml of sterilized Hoagland solution is applied to the plants in the jar. Jars are arranged randomly in growth chamber maintained at 28° C. with 12 h photoperiod. During every 7 days interval after inoculation, plants and adhering sand are carefully removed from the jars. Roots are washed in sterile phosphate buffer (pH 7.0), and measurement of root length is recorded.

Example 31

Production of Stable Dry Composition Containing Probiotic Bacteria *Lactobacillus acidophilus* (DSM-20356)

Frozen bacterial concentrate (10 g obtained from a local fermentation process) was thawed at 37° C. in a water bath and the solid content adjusted to 10% solids wet wt with distilled water). About 5 g of hydrolyzed pea protein (ultra filtrated hydrolisates, Marcor, Carlstadt, N.J.) is completely dissolved in 50 g warm water and added to the thawed bacterial culture. About 2.5 g of trehalose (Cargill Minneapolis, Minn.), about 5 g of instant Inulin, about 5 g maltodextrin DE-1 (Cargill Minneapolis, Minn.) and about 1.5 g of sodium alginate (ISP Corp., Wayne, N.J.) were uniformly mixed in dry form. The powders mixture was slowly added to the bacterial culture and mixing was carried out using a small spatula at 37° C. for 20 minutes. The slurry was then allowed to drip into a bath containing liquid nitrogen. The beads were then removed from the liquid nitrogen, placed in sealed aluminum foiled bag and stored in a deep freezer at −80° C. until dry.

For drying, the frozen beads were evenly spread on trays at a loading capacity ranging from 500 up to 1500 g/sq ft and the trays placed on shelves in a freeze drier (Model 25 SRC, Virtis, Gardiner, N.Y.). A primary liquid drying step was started by adjusting the vacuum pressure to between 2000-2700 mTORR and product temperature raised and stabilized between −10-5° C. Over time (about 10-16 h) the product temperature increased to about 20-25° C. at which point a secondary drying step initiated at maximum vacuum (150-200 mTORR) and product temperature maintained at between 30-40° C. for additional 14 hours. The formulation was completely dried and its water activity measured below 0.3 Aw. The formulation was grounded using a commercially available hammer mill and particles sieved to below 100 micron.

Figure 16:
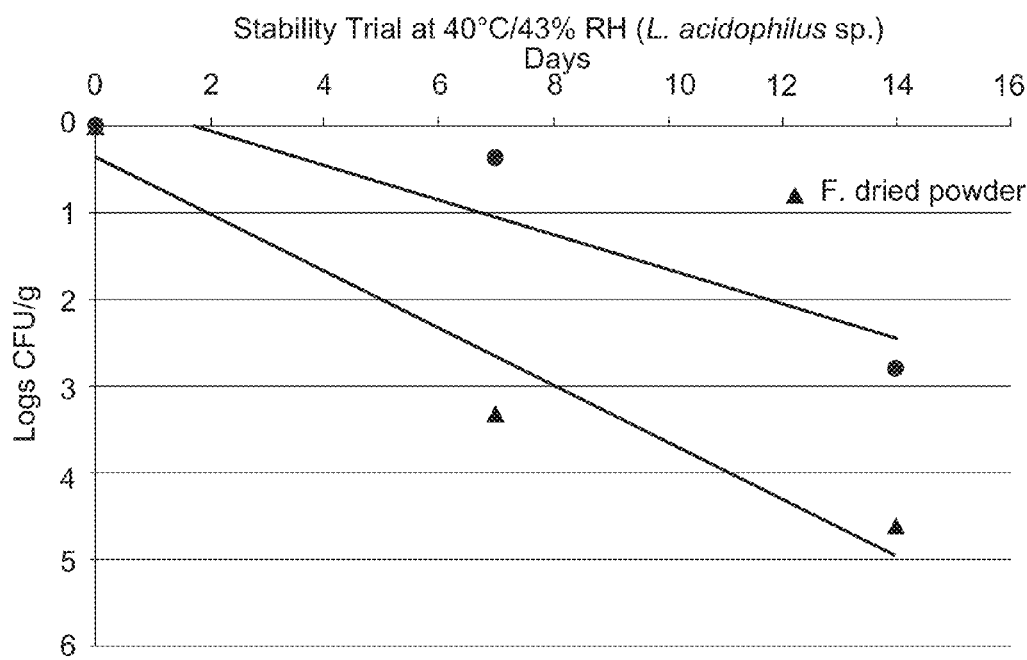
FIG. 16. Shelf storage stability at 40° C. and 43% RH of commonly freeze dried *L. acidophilus* sp. or after formulating in the composition and methods of the present invention.

The viability of the stable probiotic bacteria along with a commonly freeze dried powder of the bacterial was monitored on a weekly basis following standard procedures of dilution and plating on LMRS agar plates. FIG. 16 shows that after 14 days at 40° RH, the stability of the probiotic bacteria that formulated in the composition of the present invention was two (2) logs higher than the stability of commonly freeze dried bacteria. These results demonstrate that the stability of probiotic bacteria is dramatically improved in high humidity and non-refrigerated storage conditions when using the compositions and methods of the present invention.

Example 32

Production of Stable Dry Molten Fats Agglomerated Composition Containing Probiotic Bacteria *Lactobacillus acidophilus* (DSM-20356)

Ten (10) g of dry powder composition was produced as described in Example 31. The dry powder was placed in a beaker in a 40° C. water bath. 10 g of molten fats mixture containing eight (8) portions of cocoa butter and two (2) portions of stearate (27-Stearine, Loders Croklaan, Channahon, Ill.) were slowly added to the warm powder under mixing. The mixture was cooled down to 10° C. while mixing was continued until a visually uniform size of agglomerated powder was achieved.

Example 33

Shelf Storage Stability at 40° C. and 43% RH or 30° C. and 60% RH of a Dry Composition Containing Probiotic Bacteria *Lactobacillus rhamnosus* sp.

Figure 17:
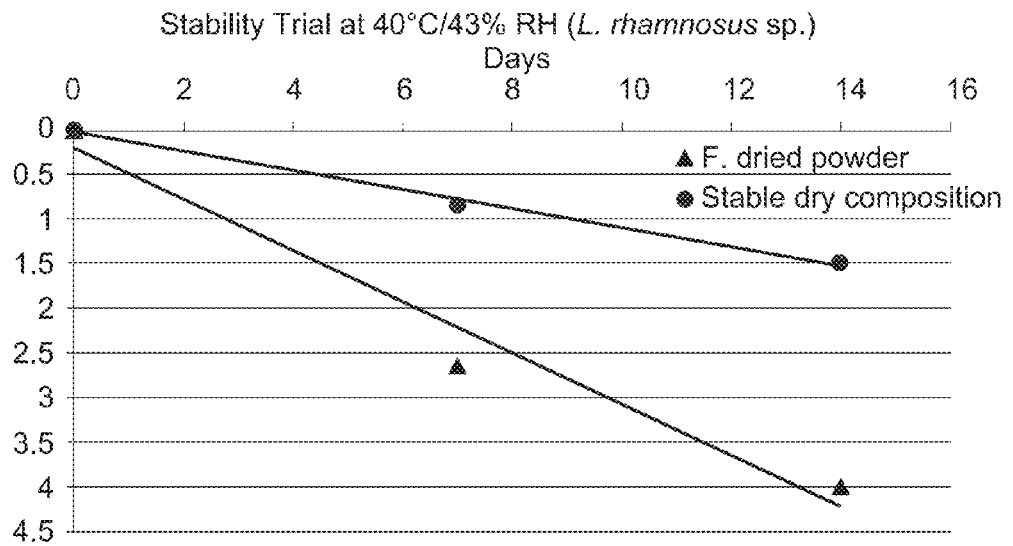
FIG. 17. Shelf storage stability at 40° C. and 43% RH and 30° C. and 60% RH commonly freeze dried *L. rhamnosus* sp. or after formulating in the composition and methods of the present invention.
Figure 17:
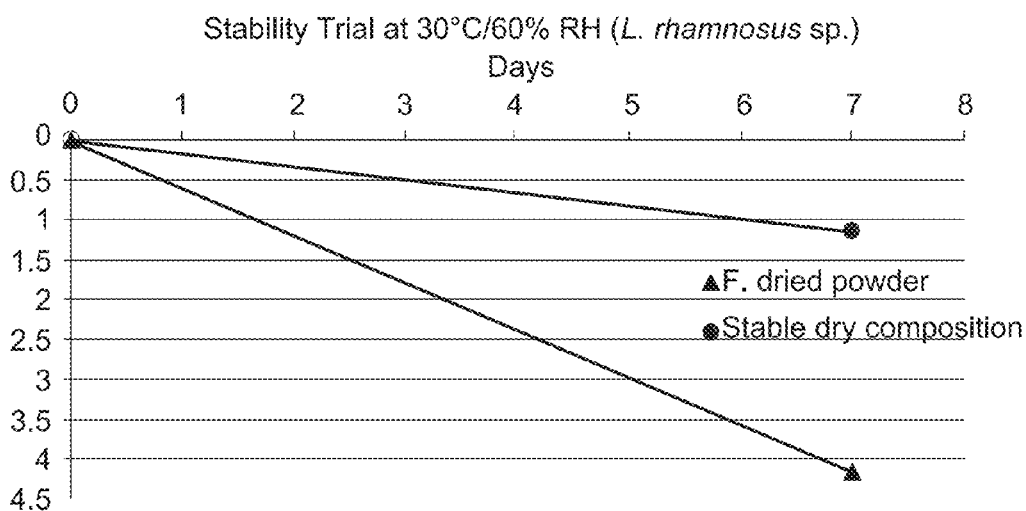

Ten (10) g of dry powder composition containing the probiotic bacterial *Lactobacillus rhamnosus* sp. (obtained from a local fermentation source) was produced as described in Example 31. The dry stable composition was placed in a desiccator and exposed to 40° C. and 43% RH or 30° C. and 60% RH. The viability of the stable probiotic along with a commonly freeze dried powder of the bacteria was monitored on a weekly basis following standard procedures of dilution and plating on LMRS agar plates. FIG. 17 shows that after 14 days at 40° C. and 43% RH, the stability of the probiotic bacteria that was formulated in the composition of the present invention was three (3) logs higher than the stability of commonly freeze dried bacteria. After 7 days at 30° C. and 60% RH, the stability of the probiotic bacteria that was formulated in the composition of the present invention was also three (3) logs higher than the stability of commonly freeze dried bacteria. These results demonstrate that the stability of probiotic bacteria is dramatically improved in high humidity non-refrigerated storage conditions when using the compositions and methods of the present invention.

Example 34

Production of Animal Feed Containing Stable Dry Composition Containing Probiotic Bacteria Against Pathogenic Microorganisms About 10 kg of commercially available animal feed for either steers or chickens is top coated in a drum tumbler with 3% oil mixture containing one portion of the ground biological material as described in Example 31 or 32 and two (2) portions of plant oil such as corn oil. The CFU count of the probiotic bacteria is 1E9/g feed. The coated feed is placed in a 43% relative humidity chamber at 40° C. and after 14 days storage in these extreme conditions; the viability loss of the probiotic bacteria is less than one (1) log of the initial CFU. Another coated feed is placed in a 33% relative humidity chamber at 30° C. and after six (6) month storage in these conditions; the viability loss of the probiotic bacteria is less than one (1) log of the initial CFU. These example demonstrates that microorganisms, such as *Lactobacillus* sp., used for treating various animals including companion animals, can be preserved in the composition and drying methods of the present invention and then coated on feeds for long term storage on shelf or for at least two (2) weeks in a feeding hopper under typical humid and temperature conditions that uncoated feed is stored.

Example 35

Production of Stable Dry Composition Containing Unicellular Fungi *S. cerevisiae*

Fresh bakery yeast paste (100 g obtained from a local distributor) is placed in a water bath at 10° C. About 50 g of hydrolyzed pea protein (ultra filtrated hydrolisates, Marcor, Carlstadt, N.J.) is completely dissolved in 500 g warm water. The solution is cooled to 10° C. and added to the yeast paste while mixing. About 25 g of sucrose (obtained from a local grocery store), about 50 g of instant Inulin, about 50 g maltodextrin DE-1 (Cargill Minneapolis, Minn.), about 12 g of sodium ascorbate (Sigma) and about 15 g of sodium alginate (ISP Corp., Wayne, N.J.) are uniformly mixed in dry form. The powders mixture is slowly added to the yeast culture and mixing is carried out at 40 RPM and 10° C. for 20 minutes. The slurry is then transferred to a vessel having a perforated bottom and allowed to drip into a bath containing liquid nitrogen. The beads are then removed from the liquid nitrogen, placed in sealed aluminum foiled bag and stored in a deep freezer at −80° C. for several weeks. Drying and milling are carried out as described in Example 31.

Example 36

Spray Drying of Stable Dry Composition Containing Unicellular Fungi *S. cerevisiae*

Yeast slurry is prepared as described in Example 34. The slurry is further diluted with cold (10° C.) distilled water to obtain a viscosity of about 1000-2000 cP. The diluted slurry is spray dried (Mobile Minor spray drier, GEA Niro Inc., Columbia, Md.), using an inlet/outlet temperature setup of 180° C./60° C.

Example 37

Coating of Corn Seeds with Stable Dry Composition Containing Unicellular Fungi

About 10 kg of commercially available corn seeds is topcoated at 40° C. in a drum tumbler with 3% molten oil mixture containing one portion of the ground biological material as described in Example 34 or Example 35 and two (2) portions of plant oil such as palm or coconut oil. The yeast CFU count is 1E8/g seed. The coated seeds are placed in a 60% relative humidity chamber at 30° C. and after three (3) months storage in these extreme conditions, the viability loss of the yeast is less than one (1) log of the initial CFU. This example demonstrates that microorganisms used as agriculture inoculums such as various strains of *Penicillium* sp. can be preserved in the composition and drying methods of the present invention and then coated on grains for long term storage under typical humid and temperature conditions that uncoated seeds are stored.

Example 38

Preparation of a Hydrogel Composition Containing Probiotic Bacteria *Bifidobacterium* sp.

Concentrated probiotic slurry of *Bifidobacterium* sp. is prepared according to Example 31. To the powders mixture, 5 g of dibasic calcium phosphate is added. The powders mixture is added to the probiotic culture under mixing followed by 5 g of gluconolactone. The slurry is allowed to harden at room temperature over the next two (2) hours to form a solid hydrogel. The firm gel is sliced to thin and long threads, using a commercially available slicer/shredder. The thin threads are directly loaded on trays in wet form or snap-frozen in liquid nitrogen and loaded on a tray at a loading capacity of 500 g/sq ft and placed in a freeze drier for drying as described in Example 31. The dry formulation is ground to fine powder using standard hammer milling equipment and sieved through 50-micron screen.

Example 39

Production of Stable Cultured Milk Containing Probiotic Bacteria

One hundred (100) gram pasteurized plain culture milk (Dannon, obtained from a local grocery store) is added with one half (0.5) gram cross-linked powder containing stable probiotic as described in Example 37. The initial CFU count in the culture milk is 1E9/g culture milk. The cultured milk is stored in a refrigerator at 4° C. for six (6) weeks. The viability loss of the probiotic bacteria in the refrigerated culture milk is less than one (1) log of the initial CFU. This example demonstrates that probiotic bacteria such as various strains of *Lactobacillus* and *Bifidobacterium* can be preserved in the composition and drying methods of the present invention. Then the probiotic bacteria in the compositions can be fully hydrated and remain active in dairy products for extended period of time under typical conditions that unpreserved probiotic bacteria will not survive.

Example 40

Stable Dry Composition Containing an Enzyme

A hydrogel formula containing 40 weight percent of phitase (Marcor, Carlstadt, N.J.) is prepared by mixing 250 g of the powder mixture as described in Example 34 and 200 g of phitase in 500 ml of water solution containing about 50 g hydrolyzed pea protein. The shredded hydrogel formulation is snap-frozen in liquid nitrogen and dried in a vacuum oven at a primary and secondary drying temperature of 50° C. For determination of loading and storage stability of the dried composition: a dry sample is accurately weighed (<100 mg) in a microcentrifuge tube. 200 μl of dimethyl sulfoxide (DMSO) is added. The formulation is dissolved in the DMSO buffer by vortexing. To this sample, 0.8 ml of a solution containing 0.05 N NaOH, 0.5% SDS and 0.075 M Citric acid (trisodium salt) is added. The tubes are sonicated for 10 min at 45° C., followed by a brief centrifugation at 5,000 rpm for 10 min. Aliquots of the clear DMSO/NaOH/SDS/Citrate solution are taken into wells of a microplate and analyzed for protein content using the Bradford assay method. The stability of the stable enzyme dry composition after exposure to 95° C. for 20 min is significantly higher than a dry enzyme without the composition of the present invention.

Example 41

Stable Dry Composition Containing a Plant Biological Control Agent

A biological control agent such as *Rhizobacteria* is prepared in dry composition according to Example 34. The effectiveness of the dry *Rhizobacteria* composition is evaluated on lettuce growth under gnotobiotic conditions. Doses of 100 mg of *Rhizobacteria* dry composition per plant are inoculated into jars with sand and planted with pre-germinated (24 h) lettuce seedlings. A nutrient dose of 5 ml of sterilized Hoagland solution is applied to the plants in the jar. Jars are arranged randomly in growth chamber maintained at 28° C. with 12 h photoperiod. During every 7 days interval after inoculation, plants and adhering sand are carefully removed from the jars. Roots are washed in sterile phosphate buffer (pH 7.0), and measurement of root length is recorded. Lettuce seedlings treated with *Rhizobacteria* composition show enhanced growth than untreated seedlings.

Example 42

Production of Tablets Containing Stable Dry Composition of the Probiotic Bacteria *Lactobacillus rhamnosus* sp.

Frozen bacterial concentrate (10 g obtained from a local fermentation process) was thawed at 37° C. in water bath and the solid content adjusted to 10% solids wet wt with distilled water. About 5 g of hydrolyzed pea protein (ultra filtrated hydrolisates, Marcor, Carlstadt, N.J.) was completely dissolved in 50 g warm water and added to the thawed bacterial culture. About 5 g of trehalose (Cargill Minneapolis, Minn.) and about 2.5 g of sodium ascorbate were uniformly mixed in dry form. Optionally, about 5 g of instant Inulin, about 5 g maltodextrin DE-1 (Cargill Minneapolis, Minn.) and about 1.5 g of sodium alginate (ISP Corp., Wayne, N.J.) were also added to form viscous slurry at a desirable viscosity of about 50,000 cP and to further enhance to glassy structure of the dry material. The powders mixture was slowly added to the bacterial culture and mixing was carried out at 37° C. for 20 minutes. The viscous bacterial suspension was then slowly dripped into a liquid nitrogen bath. The frozen beads were then removed from the liquid nitrogen, placed in a sealed aluminum foiled bag and stored in a deep freezer at −80° C. until drying.

For drying, the frozen beads were evenly spread on trays at a loading capacity ranging from 500 up to 1500 g/sq ft and the trays placed on shelves in a freeze drier (Model 25 SRC, Virtis, Gardiner, N.Y.). A primary moisture removal step was started by adjusting the vacuum pressure to between 2000-2700 mTORR and allowing the product temperature to rise and stabilizes between minus −10-5° C. Over time (about 10-16 h) the product temperature increased to about 20-25° C. at which point a secondary drying step initiated at maximum vacuum (50-200 mTORR) and product temperature maintained at between 30-45° C. for additional 14 hours. The formulation was completely dried and its water activity measured below 0.3 Aw. The formulation was milled using a coffee grinder and particles sieved to below 250 micron.

For tableting, the dry and stable probiotic composition (100 mg) was mixed with 400 mg of maltodextrin DE-1 containing 2% w/w magnesium stearate and 2% w/w hydrophilic fumed silica (AEROSIL® 200, Evonik Industries) and compressed in hand held pill press equipment (using a ¼" tablet diameter housing). Similar tablets containing commonly freeze dried powder of the probiotic bacteria (free probiotic) were also prepared and used for comparison with tablets containing protected probiotic bacteria.

Figure 18:
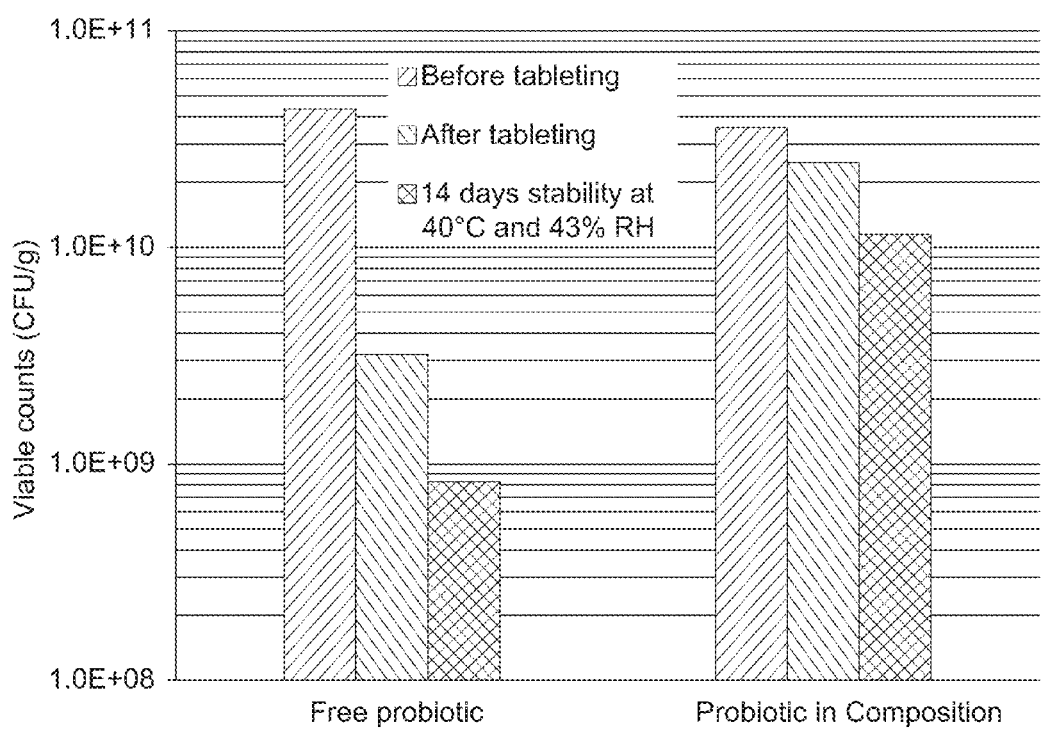
FIG. 18 demonstrates the effect of compression in tablet press on viability and storage stability at 40° C. and 43% RH of the probiotic *L. rhamnosus* stabilized and protected in the composition of the present invention.

The viability before and after tableting and during storage in 40° C. and 43% RH of the stable probiotic bacteria along with free probiotic was monitored on a weekly basis, following standard procedures of dilution and plating on LMRS agar plates. FIG. 18 shows that the free probiotic bacteria lost over a log of viability in the tableting process whereas the viability of protected bacteria remained essentially the same after the tableting process. After 14 days storage in 40° C. and 43% RH, the viability of the probiotic bacteria that formulated in the composition of the present invention, was slightly reduced by about 0.3 logs while the viability of commonly freeze dried bacteria reduced further by about 0.6 logs. These results demonstrate that the composition and methods of the present invention provide a significant protection against compression pressure and associated heat during tableting of probiotic bacteria and during storage in high humidity and non-refrigerated storage conditions.

Example 43

Preparation of Multivitamins/Probiotic Tablets Containing Stable Dry Composition of the Probiotic Bacteria *Lactobacillus rhamnosus* Sp.

The protection of the compositions and methods as disclosed herein was then further explored in tablets containing multivitamin ingredients. Ten (10) g of dry powder composition was produced as described in Example 42. For tableting, the dry and stable probiotic composition (100 mg) was mixed with 400 mg of commercially available multivitamins powder (Centrum®, Pfizer) containing 2% w/w magnesium stearate and 2% w/w hydrophilic fumed silica (AEROSIL® 200, Evonik Industries) and compressed in hand held pill press equipment (using a "A" tablet diameter housing). Similar tablets containing commonly freeze dried powder of the probiotic bacteria (free probiotic) were also prepared and used for comparison with tablets containing protected probiotic bacteria. The resultant tablets were then tested for total probiotic count. The results are shown in FIG. 19.

Figure 19:
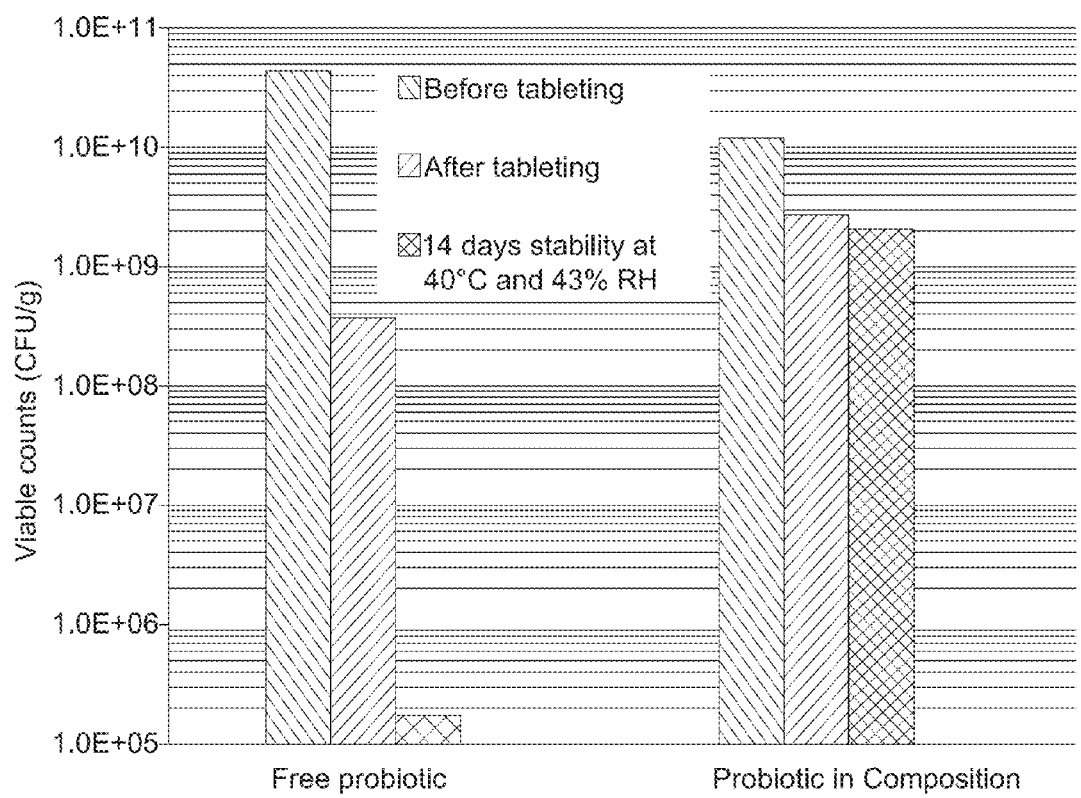
FIG. 19 shows the effect of tableting with a mixture of multivitamin and minerals and storage exposure at 40° C. and 43% RH on the viability of the probiotic *L. rhamnosus* stabilized and protected in the composition of the present invention.

As shown in FIG. 19, the free probiotic bacteria lost over two (2) logs of viability in the tableting with multivitamin ingredients process whereas the viability of protected bacteria reduced by less than a log. After 14 days storage in 40° C. and 43% RH, the viability of the probiotic bacteria that formulated in the composition of the present invention remained essentially the same while the viability of commonly freeze dried bacteria plummeted by additional three (3) logs. These results demonstrate that the composition and methods of the present invention also provide a significant protection to sensitive biological materials from other damaging compounds in the tablet mix, thereby allowing the admixing in one tablet a variety of biological materials without affecting their overall potency.

Example 44

Tableting of a Stable Dry Composition Containing Protected Enzymes

Dry and stable compositions containing a protease or a lipase (both from Sigma) were prepared as described in Example 42. The final dry compositions contained 10% protease or lipase, 40% trehalose, 20% extensively hydrolyzed pea protein, 10% sodium ascorbate. In addition, 6% sodium alginate and 14% inulin were also included in the composition.

For tableting, the dry enzyme compositions (50 mg each) were mixed with 450 mg of maltodextrin DE-1 containing 2% w/w magnesium stearate and 2% w/w hydrophilic fumed silica and compressed in hand held pill press equipment (using a ½" tablet diameter housing). Tablets containing equal amounts of both protected enzymes were also prepared by mixing and 25 mg protease and 25 mg lipase with 450 mg maltodextrin DE1 mix. Similar tablets containing dry powder of the enzyme in a free form (free enzyme or a mixture of both) were also prepared and used for comparison with tablets containing the protected enzymes.

The remaining activity of protease and lipase after tableting relative to their activity in the powder mix before tableting was determined according to methods known in the art using Azocasein and pNP-palmitate as substrates, respectively.

Figure 20:
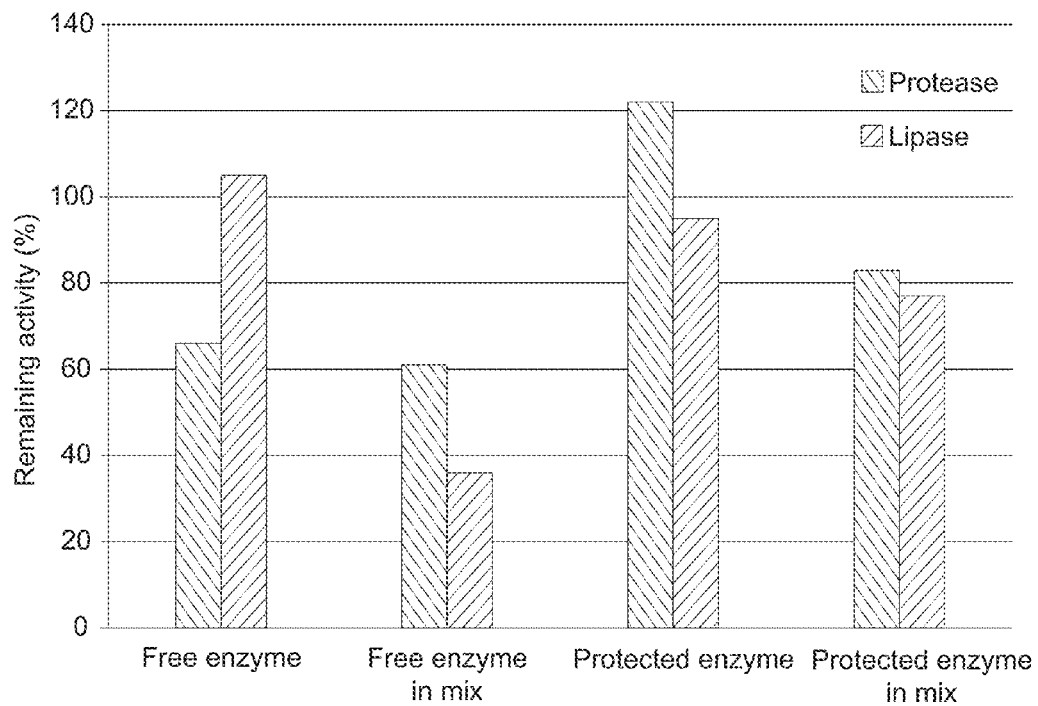
FIG. 20 illustrates the effect of compression in tablet-press on the activity of protease and lipase enzymes in a free form or protected in the composition of the present invention. The enzymes were tableted either individually or mixed in equal amount and then tableted.

As shown in FIG. 20, tableting free protease either alone or in combination with free lipase resulted in about 40% loss of activity whereas the protected protease did not lose any activity when tableted alone and only about 17% when tableted in a mix with protected lipase. Tableting free or protected lipase did not result in any significant loss of activity however, tableting free lipase in the presence of free protease resulted in 64% loss of activity, whereas tableting protected lipase in the presence of protected protease resulted in only 33% loss of activity. These results demonstrate that the composition and methods of the present invention provide a significant protection against compression pressure and associated heat during tableting of enzymes. Results also show that the composition and methods of the present invention provide protection from other digesting enzymes in the tablet mix, thereby allowing the admixing in one tablet a variety of desired enzymes without affecting their overall activity.

Example 45

Tableting of Animal Feed Containing Stable Dry Composition Containing Probiotic Bacteria Against Pathogenic Microorganisms The protection of the compositions and methods as disclosed herein is further explored in tablets containing animal feed ingredients. About 100 g of dry and stable compositions containing the probiotic bacteria *L. acidophilus* sp. is prepared and dried as described in Example 42. The final dry compositions contained 10% dry bacterial cell biomass, 54% trehalose, 20% extensively hydrolyzed pea protein, 10% sodium ascorbate. In addition, 6% sodium alginate is also included in the composition.

About 10 kg of commercially available dog food or chicken finished feed pellets is air dried over night at 40° C. and then finely ground to free flowing powder. The stable dry probiotic composition is mixed with the feed powder and compressed in hand held pill press equipment (using ⅛-½" pill diameter housings) to form about 200-2000 mg size pills containing about ten (10) billion live cells per gram feed. For chicken treatment, the probiotic feed pills is slowly poured into 100 kg of standard commercial feed while mixing. The treated finished feed is ready to feed the birds and to boost resistance to pathogens such as *salmonella*. For stability testing the probiotic pills are placed in a 43% relative humidity chamber at 40° C. and after 14 days storage in these extreme conditions, the viability loss of the probiotic bacteria is less than one (1) log of the initial CFU. This example demonstrates that microorganisms used for treating various animals including companion animals such as various *Lactobacillus* sp. can be protected in the composition and drying methods of the present invention and then compressed in a tablet press and be provided with standard feeds in a typical feeding hopper under typical humid and temperature conditions.

Example 46

Preparation of Fizzy Effervescent Beverage Tablets Containing Stable Dry Composition of Probiotic Bacteria About 10 g powder of dry and stable compositions containing the probiotic bacteria *L. acidophilus* sp. or *Bifidobacterium* sp. is prepared and dried as described in Example 42 and 45.

Effervescent tablets such as Alka Seltzer®, Fizziest or sports drinks are finely ground to free flowing powder. The stable dry probiotic composition is mixed with the effervescent powder and compressed in hand held pill press equipment (using ⅞" tablet diameter housing) to form about 2000 mg size tablets containing about ten (10) billion live cells per tablet. For stability testing the probiotic effervescent tablets are placed in a 43% relative humidity chamber at 33° C. and after 90 days storage in these extreme conditions, the viability loss of the probiotic bacteria is less than one (1) log of the initial CFU. This example demonstrates that sensitive biological materials such as live probiotic bacteria can be protected and stabilized in the composition and drying methods of the present invention and then compressed in a tablet press and stored under harsh consumption conditions of humidity and temperature.

Example 47

Preparation of Tablets Containing Stable Dry Composition of Probiotic Bacteria for Treating Vaginal Infections Such as Yeast or Bacterial Vaginosis About 15 g powder of dry and stable compositions containing the probiotic bacteria *L. acidophilus* sp. is prepared and dried as described in Examples 1 and 4.

The dry probiotic composition is blended with 74 g lactose, 10 g corn starch, 0.5 g magnesium stearate, 0.01 g sodium carboxymethylcellulose, 0.01 g polyvinylpyrrolidine and 0.01 g hydrophobic fumed silica and mixed for 15 minutes. The powdered mixture is compressed in hand held tablet press equipment. The weight of resulting tablet is about 1.5 g. Maximum tablet hardness is 6 to 8 kg. The tablet disintegrated in water in about 30 seconds.

Example 48

Production of Oil Suspension Containing Stable Dry Composition of Probiotic Bacteria *Lactobacillus acidophilus* (DSM-20356)

Frozen *L. acidophilus* concentrate (200 g obtained from a local fermentation process) was thawed at 37° C. in a water bath and added with 200 g of 3% hydrolyzed pea protein (ultra filtrated hydrolisates, Marcor, Carlstadt, N.J.) solution. The bacteria suspension was centrifuged at 4000 g for 15 min (Sorvall RC-5B, Du-Pont Company, Wilmington, Del.) and supernatant decanted. The bacteria precipitate was brought up to the original weight (200 g) with 3% hydrolyzed pea protein solution. Additional 50 g of hydrolyzed pea protein was completely dissolved in 80 g warm water, pH adjusted to 9 with 20% NaOH solution and added to the bacterial culture. Eighty five point six (85.6) g of sucrose (obtained from a local market), 30 g of Cyclodextrin-7 (Cargill Minneapolis, Minn.), 20 g sodium ascorbate (Sigma) and 15 g of sodium alginate (ISP Corp., Wayne, N.J.) were uniformly mixed in dry form. The powders mixture was slowly added to the bacterial culture and mixing was carried in a 1 qt planetary mixer (Charles Ross & Son Company, Hauppauge, N.Y.) at 37° C. for 20 minutes. The slurry was then slowly dripped into a bath containing liquid nitrogen. The frozen beads were then removed from the liquid nitrogen, placed in sealed aluminum foiled bag and stored in a deep freezer at −80° C. until drying.

For drying, the frozen beads were evenly spread on trays at a loading capacity ranging from 500 up to 1500 g/sq ft and the trays placed on shelves in a freeze drier (Model 25 SRC, Virtis, Gardiner, N.Y.). A primary drying step was started by adjusting the vacuum pressure to between 2000-2700 mTORR and product temperature raised and stabilized between −12° C. and −5° C. Over time (about 10-16 h) the product temperature increased to about 20-25° C. at which point a secondary drying step initiated at maximum vacuum (100-150 mTORR) and product temperature maintained at between 30-40° C. for additional 14 hours. The formulation was completely dried and its water activity measured below 0.3 Aw. The formulation was milled using a commercially available hammer mill and particles sieved to below 250 micron.

The viability of the stable composition of the probiotic bacteria was tested at 40° C. and 43% RH for 14 days in a dry powder form or in corn oil suspension (1 g dry powder mixed in 100 g oil) or after coating 10 g oil suspension on 45 g chicken feed pellets (the feed pellets were first acclimated in 33% RH humidity chamber for two weeks). After 14 days incubation at 40° C. and 43% RH, the probiotic bacteria lost only 0.5 logs of CFU/g when kept in a dry form, 0.34 logs when mixed in oil suspension and 0.65 logs when coated on chicken feed. These results demonstrate that the viability of the probiotic bacteria is preserved in various feed applications after 14 days exposure in high humidity and non-refrigerated storage conditions when using the compositions and methods of the present invention.

Example 49

Production of Stable Dry Composition Containing Live Phages Against *Vibrio anguillarum*

Concentrated live phages culture (100 g obtained from a manufacturer) is placed in a jacketed planetary mixer at 10° C. About 50 g of hydrolyzed pea protein (ultra filtrated hydrolisates, Marcor, Carlstadt, N.J.) is completely dissolved in 300 g warm water. The solution is cooled to 10° C. and added to the phages culture while mixing. One hundred seventy four (174) g of sucrose (obtained from a local market), 60 g of Cyclodextrin-7 (Cargill Minneapolis, Minn.), 40 g sodium ascorbate (Sigma) and 30 g of sodium alginate (ISP Corp., Wayne, N.J.) are uniformly mixed in a dry form. The powders mixture is slowly added to the phage culture and mixing is carried in a 1 qt planetary mixer at 10° C. for 20 minutes. The slurry is then slowly dripped into a bath containing liquid nitrogen. The frozen beads are then removed from the liquid nitrogen, placed in sealed aluminum foiled bag and stored in a deep freezer at −80° C. until drying. Drying and milling are carried out as described in Example 48. Ten (10) grams of dry composition powder is mixed with 100 g of fish oil and the suspension coated on 10 kg Atlantic salmon feed pellets. The coated feed is then stored in under typical warehouse storage conditions. The viability of the pages in the fish feed is preserved after 14 days exposure in high humidity and non-refrigerated storage conditions when using the compositions and methods of the present invention.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A dry stabilizing composition in an amorphous glassy state, comprising a bioactive material, one or more disaccharides at 10-50%, one or more oligosaccharides at 10-80%, one or more polysaccharides at 0.1-10%, one or more hydrolyzed proteins at 0.5-40%, and one or more carboxylic acid salts, each percentage based on the total weight of the composition, wherein the one or more oligosaccharides consist of cyclodextrin, wherein the bioactive material consists of a live microorganism, and wherein the composition exhibits less than one log loss of Colony Forming Unit per gram (CFU/g) after 14 days at 40° C. and 43% relative humidity (RH).

2. The composition of claim 1, wherein the one or more hydrolyzed proteins are selected from the group consisting of hydrolyzed casein, hydrolyzed whey protein, hydrolyzed pea protein, hydrolyzed soy protein, and a mixture thereof.

3. The composition of claim 1, wherein the one or more polysaccharides are selected from the group consisting of cellulose acetate phthalate (CAP), carboxy-methyl-cellulose, pectin, salts of alginic acid, hydroxyl propyl methyl cellulose (HPMC), methyl cellulose, carrageenan, gellan gum, guar gum, gum acacia, xanthan gum, locust bean gum, chitosan and chitosan derivatives, collagen, polyglycolic acid, starches, modified starches, and a mixture thereof.

4. The composition of claim 1, wherein the one or more disaccharides are selected from the group consisting of trehalose, sucrose, lactose, and a mixture thereof.

5. The composition of claim 1, wherein the carboxylic acid is selected from the group consisting of lactic acid, ascorbic acid, maleic acid, oxalic acid, malonic acid, malic acid, succinic acid, citric acid, gluconic acid, and glutamic acid.

6. The composition of claim 1, wherein the live microorganism is a probiotic bacterium.

7. The composition of claim 1, wherein the composition is dried by one or more processes selected from the group consisting of air drying, vacuum-drying, fluid bed drying and spray-drying.

8. A reconstituted liquid, a ground powder, a tablet, a pellet, a capsule, a food, a feed, or a coated seed product prepared with the composition of claim 1.

9. A nutraceutical, pharmaceutical agricultural or vaccine product comprising the composition of claim 1.

10. A food, food additive, animal feed, animal feed additive, nutraceutical, pharmaceutical, agricultural or vaccine product in the form of a bar, liquid formula, colloidal suspension, powder, tablet, capsule, or coated seed, prepared with the composition of claim 1.

11. The composition of claim 1, wherein the hydrolyzed proteins are plant proteins.

12. A dry stabilizing composition in an amorphous glassy state, comprising a bioactive material, one or more disaccharides at 10-50%, one or more oligosaccharides at 10-80%, one or more polysaccharides at 0.1-10%, one or more hydrolyzed proteins at 0.5-40%, and one or more carboxylic acid salts, each percentage based on the total weight of the composition, wherein the bioactive material consists of a live microorganism, wherein the composition exhibits less than one log loss of CFU/g after 14 days at 40° C. and 43% relative humidity (RH), and wherein the composition is prepared by a method comprising:
(a) combining the bioactive material with the one or more disaccharides, the one or more oligosaccharides, the one or more polysaccharides, the one or more hydrolyzed proteins, and the one or more carboxylic acid salts in an aqueous solvent to form a viscous slurry;
(b) snap-freezing the slurry in liquid nitrogen to form solid frozen particles in the form of beads, droplets or strings;
(c) primary drying the frozen particles by evaporation under vacuum at a temperature above the freezing temperature of the particles to form a primarily dried formulation; and
(d) secondary drying the primarily dried formulation at maximum vacuum and a temperature of 20° C. or higher for a time sufficient to reduce the water activity of the primarily dried formulation to below 0.3 Aw, whereby the composition is prepared.

13. The composition of claim 12, wherein the live microorganism is a probiotic bacterium.

14. The composition of claim 12, wherein the one or more disaccharides are selected from the group consisting of trehalose, sucrose, lactose, and a mixture thereof.

15. The composition of claim 12, wherein the one or more oligosaccharides are selected from the group consisting of cyclodextrins, inulin, maltodextrins, dextrans, fructo-oligosaccharides (FOS), galacto-oligosaccharides (GOS), mannan-oligosaccharides (MOS), and a mixture thereof.

16. The composition of claim 12, wherein the one or more oligosaccharides consist of cyclodextrin.

17. The composition of claim 12, wherein the one or more polysaccharides are selected from the group consisting of cellulose acetate phthalate (CAP), carboxy-methyl-cellulose, pectin, sodium alginate, salts of alginic acid, hydroxyl propyl methyl cellulose (HPMC), methyl cellulose, carrageenan, gellan gum, guar gum, gum acacia, xanthan gum, locust bean gum, chitosan and chitosan derivatives, collagen, polyglycolic acid, starches, modified starches, and a mixture thereof.

18. The composition of claim 12, wherein the one or more hydrolyzed proteins are selected from the group consisting of hydrolyzed casein, hydrolyzed whey protein, hydrolyzed pea protein, hydrolyzed soy protein, and a mixture thereof.

19. The composition of claim 12, wherein the carboxylic acid is selected from the group consisting of lactic acid, ascorbic acid, maleic acid, oxalic acid, malonic acid, malic acid, succinic acid, citric acid, gluconic acid, and glutamic acid.

20. The composition of claim 12, wherein the hydrolyzed proteins are plant proteins.

* * * * *